United States Patent
Solomon

(10) Patent No.: US 7,854,931 B2
(45) Date of Patent: Dec. 21, 2010

(54) IMMUNIZING COMPOSTION AND METHOD FOR INDUCING AN IMMUNE RESPONSE AGAINST THE BETA-SECRETASE CLEAVAGE SITE OF AMYLOID PRECURSOR PROTEIN

(75) Inventor: Beka Solomon, Herzlia Pituach (IL)

(73) Assignee: Ramot At Tel-Aviv University Ltd., Tel-Aviv (IL)

( * ) Notice: Subject to any disclaimer, the term of this patent is extended or adjusted under 35 U.S.C. 154(b) by 573 days.

(21) Appl. No.: 11/695,948

(22) Filed: Apr. 3, 2007

(65) Prior Publication Data
US 2007/0172484 A1    Jul. 26, 2007

Related U.S. Application Data

(62) Division of application No. 10/506,665, filed as application No. PCT/US03/06388 on Mar. 4, 2003, now Pat. No. 7,494,655.

(60) Provisional application No. 60/361,344, filed on Mar. 5, 2002.

(51) Int. Cl.
*A61K 39/395* (2006.01)
*C12P 21/08* (2006.01)

(52) U.S. Cl. .............. 424/139.1; 424/133.1; 424/135.1; 424/141.1; 530/387.3; 530/387.9; 530/388.1

(58) Field of Classification Search ................. None
See application file for complete search history.

(56) References Cited

U.S. PATENT DOCUMENTS

| | | | |
|---|---|---|---|
| 5,229,490 | A | 7/1993 | Tam |
| 5,387,742 | A | 2/1995 | Cordell |
| 5,721,130 | A | 2/1998 | Seubert et al. |
| 6,703,015 | B1 | 3/2004 | Solomon et al. |
| 6,919,075 | B1 | 7/2005 | Solomon et al. |
| 2002/0052311 | A1 | 5/2002 | Solomon et al. |
| 2003/0077252 | A1 | 4/2003 | Solomon et al. |
| 2004/0013647 | A1 | 1/2004 | Solomon et al. |
| 2004/0052766 | A1 | 3/2004 | Solomon et al. |
| 2005/0053575 | A1 | 3/2005 | Solomon |
| 2005/0089510 | A1 | 4/2005 | Solomon et al. |
| 2005/0152878 | A1 | 7/2005 | Solomon et al. |
| 2006/0008458 | A1 | 1/2006 | Solomon |
| 2007/0134247 | A9 | 6/2007 | Solomon |

FOREIGN PATENT DOCUMENTS

| | | |
|---|---|---|
| WO | 99/27944 A1 | 6/1999 |
| WO | 00/72880 A2 | 12/2000 |
| WO | 0118169 A2 | 3/2001 |
| WO | 01/53457 A2 | 7/2001 |
| WO | 02074243 A2 | 9/2002 |
| WO | 03/000719 A2 | 1/2003 |

OTHER PUBLICATIONS

Steinhilb et al. The protease inhibitor, MG132, blocks maturation of the amyloid precursor protein Swedish mutant preventing cleavage by beta-Secretase. J Biol Chem. Feb. 9, 2001;276(6):4476-84. Epub Nov. 17, 2000.*
U.S. Appl. No. 11/927,606, filed Oct. 29, 2007.
U.S. Appl. No. 11/929,547, filed Oct. 30, 2007.
Frenkel et al, "Towards Alzheimer's beta-amyloid vaccination," Biologicals 29(3-4):243-247 (2001).
Frenkel et al, "Immunization against Alzheimer's beta -amyloid plaques via EFRH phage administration," Proc Natl Acad Sci USA 97(21):11455-11459 (2000).
Morgan D. et al., "Abeta peptide vaccination prevents memory loss in ananimal model of Alzheimer's disease", Nature. (Dec. 28, 2000), vol. 408, pp. 982-985.
Demattos R. et al., "Peripheral anti-Abeta antibody alters CNS and plasma Abeta clearance and decreases brain Abeta burden in a mouse model of Alzheimer's disease", PNAS. (Jul. 17, 2001), vol. 98, No. 15, pp. 8850-8855.
Arbel, M., 2007. "Immunomodulation of β-secretase activity in cellular and animal models of Alzheimer's disease." Thesis, section 4.2.5.
Arbel, M., Yacoby, I., Solomon, B., 2005. "Inhibition of amyloid precursor protein processing by β-secretase through site-directed antibodies." Proc Natl Acad Sci USA 102, 7718-7723.
Arbel-Ornath, M., Becker, M., Rabinovitch-Toidman, P., Gertner, M., Solomon B., 2010. "APPβ-site antibody alleviates Aβ related pathology in Alzheimer's disease mice model." manuscript accepted for publication.
Arbel, M., Solomon, B., 2007. A Novel Immunotherapy for Alzheimer's Disease: Antibodies against the β-Secretase Cleavage Site of APP. Curr Alzheimer Res. 4, 437-445.
Bayer T.A. and Wirths O. 2010. Intracellular accumulation of amyloid-β—a predictor for synaptic dysfunction and neuron loss in Alzheimer's disease. Review article in Frontiers in Aging Neuroscience 28: 1-10.
Billings, L.M. et al. 2005. Intraneuronal Aβ causes the onset of early Alzheimer's disease-related cognitive deficits in transgenic mice. Neuron. 45:675-688.
Cataldo, A.M. et al. 1997. Increased neuronal endocytosis and protease delivery to early endosomes in sporadic Alzheimer's disease: neuropathologic evidence for a mechanism of increased β-amyloidogenesis. J. Neurosci. 17:6142-6151.
Chang, W.P., Downs, D., Huang, X.P., Da, H., Fung, K.M., Tang, J., 2007. "Amyloid-β reduction by memapsin 2 (beta-secretase) immunization." Faseb J 21, 3184-3196.

(Continued)

*Primary Examiner*—Daniel E Kolker
*Assistant Examiner*—Gregory S Emch
(74) *Attorney, Agent, or Firm*—Browdy and Neimark, PLLC

(57) ABSTRACT

The present invention is directed to an immunizing composition containing an antigenic product such as a multiple antigen peptide system (MAPS) or a filamentous bacteriophage displaying an AβPP epitope spanning the β-secretase cleavage site of AβPP and a method for inducing an immune response against the β-secretase cleavage site of AβPP using this immunizing composition. The present invention is also directed to antibodies against the β-secretase cleavage site of AβPP and their use in a method for inhibiting the formation of amyloid β.

15 Claims, 10 Drawing Sheets

OTHER PUBLICATIONS

Citron, M., Teplow, D.B., Selkoe, D.J., 1995. "Generation of amyloid β protein from its precursor is sequence specific." Neuron 14, 661-670.

Hou et al., 2009. Intracellular amyloid induces impairments on electrophysiological properties of cultured human neurons, Neuroscience Letters, 462:294-299.

Hussain, I., Powell, D., Howlett, D.R., Tew, D.G., Meek, T.D., Chapman, C., Gloger, I.S., Murphy, K.E., Southan, C.D., Ryan, D.M., Smith, T.S., Simmons, D.L., Walsh, F.S., Dingwall, C., Christie, G., 1999. "Identification of a novel aspartic protease (Asp 2) as β-secretase." Mol Cell Neurosci 14, 419-427.

Kinoshita, A., Fukumoto, H., Shah, T., Whelan, C.M., Irizarry, M.C., Hyman, B.T., 2003. "Demonstration by FRET of BACE interaction with the amyloid precursor protein at the cell surface and in early endosomes." J Cell Sci 116, 3339-3346.

Kitazume, S., Tachida, Y., Oka, R., Kotani, N., Ogawa, K., Suzuki, M., Dohmae, N., Takio, K., Saido, T.C., Hashimoto, Y., 2003. Characterization of alpha 2,6-sialyltransferase cleavage by Alzheimer's β-secretase (BACE1). J Biol Chem 278, 14865-14871.

Kitazume, S., Tachida, Y., Oka, R., Shirotani, K., Saido, T.C., Hashimoto, Y., 2001. Alzheimer's β-secretase, β-site amyloid precursor protein-cleaving enzyme, is responsible for cleavage secretion of a Golgi-resident sialyltransferase. Proc Natl Acad Sci USA 98, 13554-13559.

Laird FM, Cai H, Savonenko AV, Farah MH, He K, Melnikova T, Wen H, Chiang HC, Xu G, Koliatsos VE, Borchelt DR, Price DL, Lee HK, Wong PC. 2005. "BACE1, a major determinant of selective vulnerability of the brain to amyloid-β amyloidogenesis, is essential for cognitive, emotional, and synaptic functions." J Neurosci. 25, 11693-11709.

Lichtenthaler, S.F., Dominguez, D.I., Westmeyer, G.G., Reiss, K., Haass, C., Saftig, P., De Strooper, B., Seed, B., 2003. The cell adhesion protein P-selectin glycoprotein ligand-1 is a substrate for the aspartyl protease BACE1. J Biol Chem 278, 48713-48719.

Morgan, D., 2005. "Mechanisms of Aβ plaque clearance following passive Aβ immunization." Neurodegener Dis 2, 261-266.

Nixon, R. A., Mathews, P. M. & Cataldo, A. M. 2001. The neuronal endosomallysomal system in Alzheimer's disease. J. Alzheimer's Dis. 3, 97-107.

Ohno M, Sametsky EA, Younkin LH, Oakley H, Younkin SG, Citron M, Vassar R, Disterhoft JF. 2004. "BACE1 deficiency rescues memory deficits and cholinergic dysfunction in a mouse model of Alzheimer's disease." Neuron 41, 27-33.

Rakover, I., Arbel, M., Solomon, B., 2007. "Immunotherapy against APP β-secretase cleavage site improves cognitive function and reduces neuroinflammation in Tg2576 mice without a significant effect on brain abeta levels." Neurodegener Dis 4, 392-402.

Sinha, S., Anderson, J.P., Barbour, R., Basi, G.S., Caccavello, R., Davis, D., Doan, M., Dovey, H.F., Frigon, N., Hong, J., Jacobson-Croak, K., Jewett, N., Keim, P., Knops, J., Lieberburg, I., Power, M., Tan, H., Tatsuno, G., Tung, J., Schenk, D., Seubert, P., Suomensaari, S.M., Wang, S., Walker, D., Zhao, J., McConlogue, L., John, V., 1999. "Purification and cloning of amyloid precursor protein β-secretase from human brain." Nature 402, 537-540.

Soriano, S., Chyung, A.S., Chen, X., Stokin, G.B., Lee, V.M., Koo, E.H., 1999. "Expression of beta-amyloid precursor protein-CD3gamma chimeras to demonstrate the selective generation of amyloid β(1-40) and amyloid β(1-42) peptides within secretory and endocytic compartments." J Biol Chem 274, 32295-32300.

Vassar et al., 1999, β-secretase cleavage of Alzheimer's Amyloid protein by the transmembrane aspartic protease BACE, Science, 286:735-741.

Wilcock, D.M., Rojiani, A., Rosenthal, A., Subbarao, S., Freeman M.J., Gordon, M.N., Morgan, D., 2004. "Passive immunotherapy against Aβ in aged APP-transgenic mice reverses cognitive deficits and depletes parenchymal amyloid deposits in spite of increased vascular amyloid and microhemorrhage." J Neuroinflammation 1, 24.

Willem M, Garratt AN, Novak B, Citron M, Kaufmann S, Rittger A, DeStrooper B, Saftig P, Birchmeier C, Haass C., 2006. "Control of peripheral nerve myelination by the βsecretase BACE1," Science 314, 664-666.

Yan, R., Bienkowski, M.J., Shuck, M.E., Miao, H., Tory, M.C., Pauley, A.M., Brashier, J.R., Stratman, N.C., Mathews, W.R., Buhl, A.E., Carter, D.B., Tomasselli, A.G., Parodi, L.A., Heinrikson, R.L., Gurney, M.E., 1999. "Membrane-anchored aspartyl protase with Alzheimer's disease βsecretase activity." Nature 402, 533-537.

* cited by examiner

FIG. 1

```
              β
  -6     -3   -1 | 1                11
...I S E V K M | D A E F R H D S G  Y E V H H Q K L V F F...
              L
              ↑
              |
           P₁ position
```

IMMUNIZING COMPOSTION AND METHOD FOR INDUCING AN IMMUNE RESPONSE AGAINST THE BETA-SECRETASE CLEAVAGE SITE OF AMYLOID PRECURSOR PROTEIN

CROSS-REFERENCE TO RELATED APPLICATIONS

The present application is a divisional of application Ser. No. 10/506,665, filed Sep. 7, 2004, which is a 371 national stage of PCT/US03/006388, filed Mar. 4, 2003, which claims benefit of U.S. provisional application No. 60/361,344, filed Mar. 5, 2002. The entire contents of these applications are incorporated herein by reference.

BACKGROUND OF THE INVENTION

1. Field of the Invention

The present invention relates to an immunizing composition and method for inducing an immune response against β-secretase cleavage site of amyloid precursor protein. The present invention further relates to antibodies raised or generated against the β-secretase cleavage site of amyloid precursor protein and the use thereof in passive immunization.

2. Description of the Related Art

Amyloid Precursor Protein and β-Secretase:

The extracellular deposition of short amyloid peptides in the brains of patients is thought to be a central event in the pathogenesis of Alzheimer's disease. Evidence that amyloid may play an important role in the early pathogenesis of AD comes primarily from studies of individuals affected by the familial form of AD (FAD) or by Down's syndrome. The generation of amyloid β peptide (Aβ) occurs via a regulated cascade of cleavage in its precursor protein, AβPP (amyloid precursor protein). At least three enzymes are responsible for AβPP proteolysis and have been tentatively named α, β, and γ secretase. The recent identification of several of these secretases is a major leap in understanding how these secretases regulate amyloid peptide formation. One of the main therapeutic goals is the inhibition of secretases that produce Aβ from the large precursor protein. The theoretical specificity and tractability of protease targets suggest that it should be possible to generate secretase-specific protease inhibitors that penetrate the blood brain barrier. Many studies using new knowledge of the ability of the β-secretase enzyme (BACE) to identify inhibitors by screening or rational design approaches are already underway (U.S. Pat. Nos. 5,744,346; 5,942,400; 6,221,645 B1; 6,313,268 B1; and published PCT applications WO 00/47618, WO 98/21589, and WO 96/40885). At this point, there is no evidence of additional functions of Aβ, so there are no serious concerns about reduction of this metabolite. Both β- and γ-secretases are present in many different cells in the body and it is reasonable to assume that they have substrates in addition to AβPP. Consequently, complete inhibition of one of these enzymes might result in toxicity problems, particularly under the chronic treatment conditions that would presumably be required. At the mRNA level, BACE is expressed widely in the human brain. Expression is also high in the pancreas, although enzymatic activity in this tissue is low. Apart from AβPP cleavage, it is not known if BACE possesses other activity and so it is too early to predict what toxicity β-secretase inhibitors may have.

Proteolytic processing of the amyloid precursor protein (AβPP) generates amyloid β (Aβ) peptide which is thought to be causal for the pathology and subsequent cognitive decline in Alzheimer's disease. To initiate Aβ formation, β-secretase cleaves AβPP at the N-terminus of Aβ to release APPsβ, an approximately 100-kD soluble N-terminal fragment, and C99, a 12-kD C-terminal fragment which remains membrane bound. The exact site of β-secretase cleavage has been determined (FIG. 1). Amyloid plaque Aβ starts at Asp1 and this cleavage site is therefore of major interest. Cleavage by β-secretase at the amino terminus of the Aβ peptide sequence, between residues 671 and 672 of AβPP, leads to the generation and extracellular release of β-cleaved soluble AβPP, and a corresponding cell-associated carboxy-terminal fragment.

One of the familial AD families was shown to have a mutation in AβPP that coincided with the predicted cleavage site of β-secretase. This double mutation, first identified in a Swedish pedigree, was also found to mechanistically result in overproduction of Aβ peptide relative to wild sequence when it was transfected into cells, suggesting that it was a better substrate for the β-secretase enzyme. This prediction has recently been borne out to be true. A Met to Leu substitution at the Pl position of APP, found in the "Swedish" familial AD mutation which causes early-onset AD, dramatically enhances β-secretase cleavage, but many other substitutions (for example, Met to Val) decrease β-secretase cleavage. These findings demonstrated the presence of a β-secretase activity responsible for a cleavage event that liberated the N terminus of Aβ peptide and showed the process was secretory rather than lysosomal, the favored hypothesis at the time.

Blood Brain Barrier:

The blood-brain barrier (BBB) (Johansson, 1992; Ermisch, 1992; Schlosshauer, 1993) is formed by a monolayer of tightly connected microvascular endothelial cells with anionic charges. This layer separates two fluid-containing compartments: the blood plasma (BP) and extracellular fluid (ECF) of the brain parenchyma, and is surrounded by astroglial cells of the brain. One of the main functions of the BBB is to regulate the transfer of components between the BP and the ECF. The BBB limits free passage of most agent molecules from the blood to the brain cells.

In general, large molecules of high polarity, such as peptides, proteins, (e.g., enzymes, growth factors and their conjugates, oligonucleotides, genetic vectors and others) do not cross the BBB. Therefore poor agent delivery to the CNS limits the applicability of such macromolecules for the treatment of neurodegenerative disorders and neurological diseases.

Several delivery approaches of therapeutic agents to the brain circumvent the BBB. Such approaches utilize intrathecal injections, surgical implants (Ommaya, 1984 and U.S. Pat. No. 5,222,982) and interstitial infusion (Bobo et al., 1994). These strategies deliver an agent to the CNS by direct administration into the cerebrospinal fluid (CSF) or into the brain parenchyma (ECF).

Drug delivery to the central nervous system through the cerebrospinal fluid is achieved by means of a subdurally implantable device named after its inventor, the "Ommaya reservoir". The reservoir is used mostly for localized post-operative delivery of chemotherapeutic agents in cancers. The drug is injected into the device and subsequently released into the cerebrospinal fluid surrounding the brain. It can be directed toward specific areas of exposed brain tissue which then adsorb the drug. This adsorption is limited since the drug does not travel freely. A modified device developed by Ayub Ommaya, whereby the reservoir is implanted in the abdominal cavity and the injected drug is transported by cerebrospinal fluid (taken from and returned to the spine) all the way to the ventricular space of the brain, is used for agent administration.

Diffusion of macromolecules to various areas of the brain by convection-enhanced delivery is another method of administration circumventing the BBB. This method involves: a) creating a pressure gradient during interstitial infusion into white matter to generate increased flow through the brain interstitium (convection supplementing simple diffusion); b) maintaining the pressure gradient over a lengthy period of time (24 hours to 48 hours) to allow radial penetration of the migrating compounds (such as: neurotrophic factors, antibodies, growth factors, genetic vectors, enzymes, etc.) into the gray matter; and c) increasing drug concentrations by orders of magnitude over systemic levels. Through their direct infusion into the brain parenchyma, the site-specific biomolecular complexes of U.S. Pat. No. 6,005,004 deliver the agent to neuronal or glial cells, as needed, and be retained by these cells. Moreover, the site-specific complexes containing neuronal targeting or internalization moieties are capable of penetrating the neuronal membrane and internalizing the agent.

Another strategy to improve agent delivery to the CNS is by increasing the agent absorption (adsorption and transport) through the BBB and their uptake by the cells (Broadwell, 1989; Pardridge et al., 1990; Banks et al., 1992; and Pardridge, edited by Vranic et al., 1991. The passage of agents through the BBB to the brain can be enhanced by improving either the permeability of the agent itself or by altering the characteristics of the BBB. Thus, the passage of the agent can be facilitated by increasing its lipid solubility through chemical modification, and/or by its coupling to a cationic carrier, or still by its covalent coupling to a peptide vector capable of transporting the agent through the BBB. Peptide transport vectors are also known as BBB permeabilizer compounds (U.S. Pat. No. 5,268,164).

Phage Display:

Combinatorial phage display peptide libraries provide an effective means to study protein:protein interactions. This technology relies on the production of very large collections of random peptides associated with their corresponding genetic blueprints (Scott et al, 1990; Dower, 1992; Lane et al, 1993; Cortese et al, 1994; Cortese et al, 1995; Cortese et al, 1996). Presentation of the random peptides is often accomplished by constructing chimeric proteins expressed on the outer surface of filamentous bacteriophages such as M13, fd and f1. This presentation makes the repertoires amenable to binding assays and specialized screening schemes (referred to as biopanning (Parmley et al, 1988)) leading to the affinity isolation and identification of peptides with desired binding properties. In this way peptides that bind to receptors (Koivunen et al, 1995; Wrighton et al, 1996; Sparks et al, 1994; Rasqualini et al, 1996), enzymes (Matthews et al, 1993; Schmitz et al, 1996) or antibodies (Scott et al, 1990; Cwirla et al, 1990; Felici et al, 1991; Luzzago et al, 1993; Hoess et al, 1993; Bonnycastle et al, 1996) have been efficiently selected.

Filamentous bacteriophages are nonlytic, male specific bacteriophages that infect *Escherichia coli* cells carrying an F-episome (for review, see Model et al, 1988). Filamentous phage particles appear as thin tubular structures 900 nm long and 10 nm thick containing a circular single stranded DNA genome (the +strand). The life cycle of the phage entails binding of the phage to the F-pilus of the bacterium followed by entry of the single stranded DNA genome into the host. The circular single stranded DNA is recognized by the host replication machinery and the synthesis of the complementary second DNA strand is initiated at the phage ori(−) structure. The double stranded DNA replicating form is the template for the synthesis of single-stranded DNA circular phage genomes, initiating at the ori(+) structure. These are ultimately packaged into virions and the phage particles are extruded from the bacterium without causing lysis or apparent damage to the host.

Peptide display systems have exploited two structural proteins of the phage; pIII protein and pVIII protein. The pIII protein exists in 5 copies per phage and is found exclusively at one tip of the virion (Goldsmith et al, 1977). The N-terminal domain of the pIII protein forms a knob-like structure that is required for the infectivity process (Gray et al, 1981). It enables the adsorption of the phage to the tip of the F-pilus and subsequently the penetration and translocation of the single stranded phage DNA into the bacterial host cell (Holliger et al, 1997). The pIII protein can tolerate extensive modifications and thus has been used to express peptides at its N-terminus. The foreign peptides have been up to 65 amino acid residues long (Bluthner et al, 1996; Kay et al, 1993) and in some instances even as large as full-length proteins (McCafferty et al, 1990; McCafferty et al, 1992) without markedly affecting pIII function.

The cylindrical protein envelope surrounding the single stranded phage DNA is composed of 2700 copies of the major coat protein, pVIII, an α-helical subunit which consists of 50 amino acid residues. The pVIII proteins themselves are arranged in a helical pattern, with the α-helix of the protein oriented at a shallow angle to the long axis of the virion (Marvin et al, 1994). The primary structure of this protein contains three separate domains: (1) the N-terminal part, enriched with acidic amino acids and exposed to the outside environment; (2) a central hydrophobic domain responsible for: (i) subunit:subunit interactions in the phage particle and (ii) transmembrane functions in the host cell; and (3) the third domain containing basic amino acids, clustered at the C-terminus, which is buried in the interior of the phage and is associated with the phage-DNA. pVIII is synthesized as a precoat protein containing a 23 amino acid leader-peptide, which is cleaved upon translocation across the inner membrane of the bacterium to yield the mature 50-residue transmembrane protein (Sugimoto et al, 1977). Use of pVIII as a display scaffold is hindered by the fact that it can tolerate the addition of peptides no longer than 6 residues at its N-terminus (Greenwood et al, 1991; Iannolo et al, 1995). Larger inserts interfere with phage assembly. Introduction of larger peptides, however, is possible in systems where mosaic phages are produced by in vivo mixing the recombinant, peptide-containing, pVIII proteins with wild type pVIII (Felici et al, 1991; Greenwood et al, 1991; Willis et al, 1993). This enables the incorporation of the chimeric pVIII proteins at low density (tens to hundreds of copies per particle) on the phage surface interspersed with wild type coat proteins during the assembly of phage particles. Two systems have been used that enable the generation of mosaic phages; the "type 8+8" and "type 88" systems as designated by Smith (Smith, 1993).

The "type 8+8" system is based on having the two pVIII genes situated separately in two different genetic units (Felici et al, 1991; Greenwood et al, 1991; Willis et al, 1993). The recombinant pVIII gene is located on a phagemid, a plasmid that contains, in addition to its own origin of replication, the phage origins of replication and packaging signal. The wild type pVIII protein is supplied by superinfecting phagemid-harboring bacteria with a helper phage. In addition, the helper phage provides the phage replication and assembly machinery that package both the phagemid and the helper genomes into virions. Therefore, two types of particles are secreted by such bacteria, helper and phagemid, both of which incorporate a mixture of recombinant and wild type pVIII proteins.

The "type 88" system benefits by containing the two pVIII genes in one and the same infectious phage genome. Thus, this obviates the need for a helper phage and superinfection. Furthermore, only one type of mosaic phage is produced.

The phage genome encodes 10 proteins (pI through pX) all of which are essential for production of infectious progeny (Felici et al, 1991). The genes for the proteins are organized in two tightly packed transcriptional units separated by two non-coding regions (Van Wezenbeek et al, 1980). One non-coding region, called the "intergenic region" (defined as situated between the pIV and pII genes) contains the (+) and the (−) origins of DNA replication and the packaging signal of the phage, enabling the initiation of capsid formation. Parts of this intergenic region are dispensable (Kim et al, 1981; Dotto et al, 1984). Moreover, this region has been found to be able to tolerate the insertion of foreign DNAs at several sites (Messing, 1983; Moses et al, 1980; Zacher et al, 1980). The second non-coding region of the phage is located between the pVIII and pIII genes, and has also been used to incorporate foreign recombinant genes as was illustrated by Pluckthun (Krebber et al, 1995).

to the 70-94% purity levels common in the solid-phase synthesis of peptides. The phage presents an easily renewable source of antigen, as additional material can be obtained by growth of bacterial cultures.

Immunization with the EFRH (SEQ ID NO:2) epitope displaying phage may, in a short period of time, raise the high concentration of high affinity (IgG) antibodies able to prevent the formation of β-amyloid and to minimize further toxic effects. The level of antibody in the sera was found to be related to the number of peptide copies per phage (Frenkel et al., 2000b).

The antibodies resulting from EFRH (SEQ ID NO:2) phage immunization are similar regarding their immunological properties to antibodies raised by direct injection with whole amyloid β (Table 1). These antibodies recognize the full length Aβ-peptide (1-40) and exhibit anti-aggregating properties as antibodies raised against whole Aβ peptide and/or amyloid β (Frenkel et al., 2000b, 2001). The high immunogenicity of filamentous phages enables the raising of antibodies against self-antigens. Immunization of guinea pigs with EFRH (SEQ ID NO:2) phage as an antigen, in which the Aβ peptide sequence is identical to that in humans, resulted in the production of self-antibodies (Frenkel et al., 2001).

TABLE 1

Competitive inhibition by various peptides within Aβ of serum antibody raised against f88-EFRH compared to amyloid anti-aggregating antibody*.

| PEPTIDE | RESIDUES | MICE SERUM | anti-aggregating antibody*. |
|---|---|---|---|
| FRH | (residues 4-6 of Aβ) | ~$10^{-3}$ M | $3 \times 10^{-3}$ M |
| EFRH | (residues 3-6 of Aβ; SEQ ID N0: 2) | $6.0 \times 10^{-6}$ M | $3 \times 10^{-6}$ M |
| DAEFRH | (residues 1-6 of Aβ; residues 1-6 of SEQ ID NO: 3) | $3.0 \times 10^{-6}$ M | $8 \times 10^{-7}$ M |
| DAEFRHD | (residues 1-7 of Aβ; residues 1-7 of SEQ ID NO: 3) | $5.0 \times 10^{-6}$ M | $9 \times 10^{-7}$ M |
| DAEFRHDSG | (residues 1-9 of Aβ; SEQ ID NO: 3) | $5.0 \times 10^{-6}$ M | $1 \times 10^{-6}$ M |
| Aβ(1-40) | | $3.0 \times 10^{-6}$ M | $8 \times 10^{-7}$ M |
| WVLD | (SEQ ID NO: 4) | Nd ** | Nd ** |

*Frenkel et. al. 1998
** $IC_{50}$ value of less than $10^{-2}$ M which cannot be detected by ELISA assay.

Immunization with Phage Display:

Small synthetic peptides, consisting of epitopes, are generally poor antigens requiring the chemical synthesis of a peptide and need to be coupled to a large carrier, but even then they may induce a low affinity immune response. An immunization procedure for raising anti-AβP antibodies, using as antigen the filamentous phages displaying only EFRH peptide, was developed in the laboratory of the present inventor (Frenkel et al., 2000 and 2001). Filamentous bacteriophages have been used extensively in recent years for the 'display' on their surface of large repertoires of peptides generated by cloning random oligonucleotides at the 5' end of the genes coding for the phage coat protein (Scott and Smith, 1990; Scott, 1992). As recently reported, filamentous bacteriophages are excellent vehicles for the expression and presentation of foreign peptides in a variety of biologicals (Greenwood et al., 1993; Medynski, 1994). Administration of filamentous phages induces a strong immunological response to the phage effects systems (Willis et al., 1993; Meola et al., 1995). Phage coat proteins pIII and pVIII discussed above are proteins that have been often used for phage display. The recombinant filamentous phage approach for obtaining specific peptide antigens has a major advantage over chemical synthesis, as the products obtained are the result of the biological fidelity of translational machinery and are not subject The above data demonstrated that a recombinant bacteriophage displaying a self-epitope can be used as a vaccine to induce autoantibodies for disease treatment. Filamentous phages are normally grown using a laboratory strain of E. coli, and although the naturally occurring strain may be different, it is reasonable to assume that delivery of phage into the gut will result in infection of the natural intestinal flora. The laboratory of the present inventor has found that UV inactivated phages are as immunogenic as their infective counterparts. There is evidence of long lasting filamentous phages in the guts of the immunized animals that may explain the long lasting immune response found in pIII immunized mice (Zuercher et al., 2000).

Due to the high antigenicity of the phage, administration can be given by the intranasal route, which is the easiest way for immunization without any use of adjuvant. As olfactory changes are proposed to play a role in Alzheimer's disease (Murphy, 1999) mucosal immunization is an effective induction of specific Aβ IgA antibodies for preventing local pathologic effect of the disease.

The efficacy of phage-EFRH antigen in raising anti-aggregating β-amyloid antibodies (Solomon and Frenkel, 2000) versus whole β-amyloid shows that:

a. the high immunogenicity of the phage enables production of high titer of IgG antibodies in a short period of weeks without need of adjuvant administration;

b. self-expression of the antigen led to long-lasting immunization;

c. the key role of the EFRH epitope in β-amyloid formation and its high immunogenicity led to anti-aggregating antibodies which recognize whole β-amyloid peptide, substituting the use of β-amyloid fibrils.

Antibody Engineering:

Antibody engineering methods were applied to minimize the size of mabs (135-900 kDa) while maintaining their biological activity (Winter et al., 1994). These technologies and the application of the PCR technology to create large antibody gene repertoires make antibody phage display a versatile tool for isolation and characterization of single chain Fv (scFv) antibodies (Hoogenboom et al., 1998). The scFvs can be displayed on the surface of the phage for further manipulation or may be released as a soluble scFv (~25 kd) fragment.

The laboratory of the present inventor engineered an scFv which exhibits anti-aggregating properties similar to the parental IgM molecule (Frenkel et al., 2000a). For scFv construction, the antibody genes from the anti-AβP IgM 508 hybridoma were cloned. The secreted antibody showed specific activity toward the AβP molecule in preventing its toxic effects on cultured PC 12 cells. Site-directed single-chain Fv antibodies are the first step towards targeting therapeutic antibodies into the brain via intracellular or extracellular approaches.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides an immunizing composition containing an immunizing effective amount of an antigenic product which induces an immune response against the β-secretase cleavage site of amyloid precursor protein (AβPP).

The present invention also provides a method for inducing an immune response against the β-secretase cleavage site of AβPP which involves administering the immunizing composition according to the present invention to a subject/patient in need thereof.

Further provided by the present invention is a molecule comprising the antigen binding portion of an antibody against the β-secretase cleavage site of AβPP. This molecule according to the present invention can be used in a method for blocking β-secretase cleavage of AβPP.

A preferred embodiment of the molecule according to the present invention is a single chain antibody, which when displayed on the surface of a filamentous bacteriophage display vehicle can be used in a method for inhibiting the formation of amyloid β according to the present invention.

BRIEF DESCRIPTION OF THE DRAWINGS

FIG. 1 shows the amino acid sequence (SEQ ID NO:1) surrounding the β-secretase cleavage site on AβPP, where the cleavage is between Met(M) and Asp(D), designated residues 0 and 1 based on the cleavage site and where residue 0 ($P_1$ position) is normally Met but is found to be Leu in the "Swedish" familial AD mutation.

FIG. 2A), ISEVKLDA (residues 1 to 8 of SEQ ID NO:1, where residue 6 is Leu; FIG. 2B), VKMDAEFRH (SEQ ID NO:5; FIG. 2C) antigenic peptide sequence.

DETAILED DESCRIPTION OF THE INVENTION

Figure 2A:
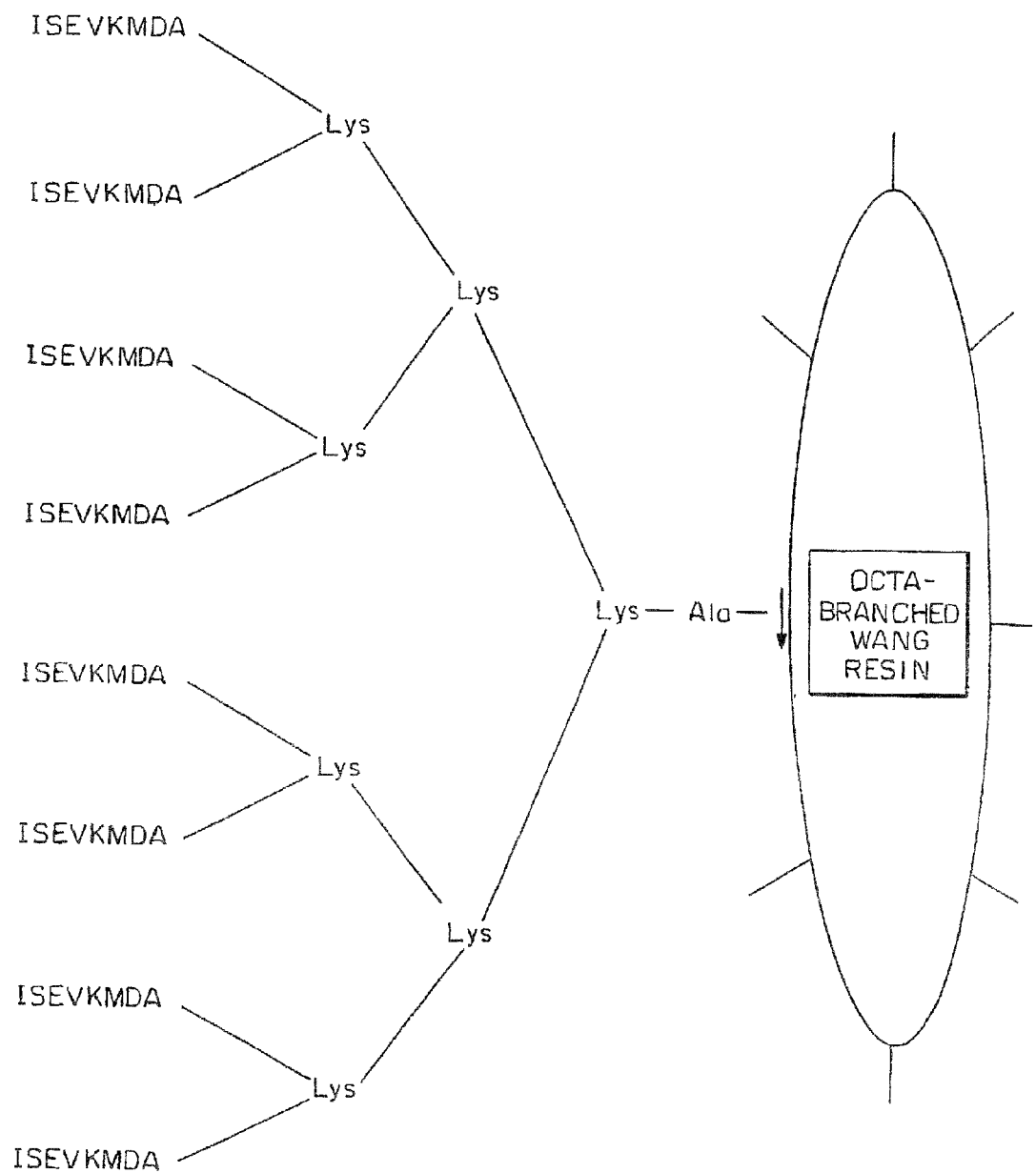
FIGS. 2A-2C show schematic representations of embodiments of multiple antigenic peptide (MAP) on octa-branched homo Wang resin according to the present invention. The arrow represents the cleavage site and the ISEVKMDA (residues 1 to 8 of SEQ ID NO:1, where residue 6 is Met.

β-secretase cleavage generates the free N-terminus of Aβ and is therefore considered the first critical step in amyloid formation. To avoid the possible problems of inhibiting the enzyme per se, which could lead to "unknown" effects, the present inventor developed a novel approach to block β-secretase cleavage of AβPP by generating anti-AβPP antibodies capable of blocking the cleavage site of β-secretase on AβPP to inhibit the in vivo formation of Aβ and thus inhibit or prevent the development of Alzheimer's disease.

The present invention is directed to a vaccine, which is also referred herein as an immunizing composition, containing an immunizing effective amount of an antigenic product that induces an immune response against the β-secretase cleavage site of AβPP, and to a method of using this immunizing composition for inducing an immune response against the β-secretase cleavage site of AβPP. This method for inducing an immune response against the β-secretase cleavage site of AβPP involves administering the immunizing composition according to the present invention to a subject/patient in need thereof.

The present invention is further directed to a method for passive immunization by administering a viral display vehicle exposing on its surface at least an antigen-binding (immunological) portion of an antibody which can bind to an AβPP epitope spanning the β-secretase cleavage site of AβPP to inhibit the formation of Aβ by blocking β-secretase cleavage of AβPP. This passive immunity may be of exceptionally long duration if the display vehicle employed is capable of replicating within the recipient/patient.

For purposes of this specification and the accompanying claims, the terms "patient", "subject" and "recipient" are used interchangeably. They include humans and other mammals which are the object of either prophylactic, experimental, or therapeutic treatment. Also, the terms "amyloid β peptide"

and "β amyloid peptide" are synonymous with "β-amyloid peptide", "βAP", "βA", and "Aβ". All of these terms refer to a plaque forming peptide derived from amyloid precursor protein (AβPP).

As used herein, the term "treating" includes substantially inhibiting, slowing or reversing the progression of a disease, substantially ameliorating clinical symptoms of a disease or substantially preventing the appearance of clinical symptoms of a disease.

The term "immune response" or its equivalent "immunological response" refers to the development of a beneficial humoral (antibody mediated) and/or a cellular (mediated by antigen-specific T cells or their secretion products) response directed against an AβPP epitope spanning the β-secretase cleavage site of AβPP in a recipient patient. Such a response can be an active response induced by administration of immunogen or a passive response induced by administration of antibody. A cellular immune response is elicited by the presentation of polypeptide epitopes in association with Class I or Class II MHC molecules, to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity.

As used herein "active immunity" refers to any immunity conferred upon a subject by administration of an antigen.

As used herein "passive immunity" refers to any immunity conferred upon a subject without administration of an antigen. "Passive immunity" therefore includes, but is not limited to, administration of a replicating display vehicle which includes an antigen-binding/immunological portion of an antibody presented on its surface to a recipient. Although replication of such a vehicle is active, the immune response is passive from the standpoint of the recipient.

For purposes of this specification and the accompanying claims, the terms "epitope" and "antigenic determinant" are used interchangeably to refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3H$-thymidine incorporation by primed T cells in response to an epitope (Burke et al., 1994), by antigen-dependent killing (cytotoxic T lymphocyte assay, Tigges et al.) or by cytokine secretion.

Preferred embodiments of the antigenic product used in the immunizing composition according to the present invention to induce an immune response against the β-secretase cleavage site of AβPP include (1) an antigen structurally based on multiple peptide antigen system (MAPs), a dendritic polymer system, in which antigenic peptides representing the β-secretase cleavage sites are covalently bound to the branches that radiate from a core molecule, and (2) a viral display vehicle displaying an AβPP epitope spanning the β-secretase cleavage site of AβPP on its surface.

The antigenic product used in a preferred embodiment of the present invention which is structurally based on a dendritic polymer is characterized by a higher concentration of functional groups per unit of molecular volume than for ordinary polymers. Generally, dendritic polymers are based upon two or more identical branches originating from a core molecule having at least two functional groups. Such polymers have been described by Denkewalter et al. in U.S. Pat. No. 4,289,872 and by Tomalia et al. in several U.S. Patents, including U.S. Pat. Nos. 4,599,400 and 4,507,466. Other polymers of the class have been described by Erickson in U.S. Pat. No. 4,515,920. The polymers are often referred to as dendritic polymers because their structure may be symbolized as a tree with a core trunk and several branches. Unlike a tree, however, the branches in dendritic polymers are all substantially identical. This dendrite system has been termed the multiple antigen peptide system (MAPS), which is the commonly used name for a combination antigen/antigen carrier that is composed of two or more, usually identical, antigenic molecules covalently attached to a dendritic core which is composed of principal units which are at least bifunctional. Each bifunctional unit in a branch provides a base for added growth. The dendritic core of a multiple antigen peptide system can be composed of lysine molecules and confers a high immunogenicity to the whole antigen. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen (MAP; FIG. 2). The process can be repeated to form fourth or even higher generations of molecules. With each generation, the number of free amino groups increases geometrically and can be represented by $2^n$, where n is the number of the generation. Alternatively, the second generation molecule having four free amino groups can be used to form a tetravalent MAP, i.e., a MAP having four peptides covalently linked to the core. Many other molecules, including e.g., aspartic acid and glutamic acid, both of which have two carboxyl groups and one amino group to produce polyaspartic or polyglutamic acids with $2^n$ free carboxyl groups, can be used to form the dendritic core of a multiple antigen peptide system.

As will be apparent from the discussion hereinafter, some of the carrier or core molecules used to form the product of the present invention are of a molecular weight such that they might not usually be regarded as polymers. However, since their basic structure is similar to dendritic polymers, it is convenient to describe them as such. Therefore the term "dendritic polymer" will be sometimes used herein to define the product of the invention. The term includes carrier molecules which are sufficiently large to be regarded as polymers as well as those which may contain as few as three monomers.

The necessary chemistry for performing the synthesis of dendritic polymers is known and available. With amino acids, the chemistry for blocking functional groups which should not react and then removing the blocking groups when it is desired that the functional groups should react has been described in detail in numerous patents and articles in the technical literature. The dendritic polymers and the entire MAP can be produced on a resin as in the Merrifield synthesis and then removed from the polymer. Tomalia utilized ammonia or ethylenediamine as the core molecule. In this procedure, the core molecule is reacted with an acrylate ester by Michael addition and the ester groups removed by hydrolysis. The resulting first generation molecules contain three free carboxyl groups in the case of ammonia and four free carboxyl groups when ethylenediamine is employed. Tomalia extends the dendritic polymer with ethylenediamine followed by another acrylic ester monomer, and repeats the sequence until the desired molecular weight is attained. It will, however, be readily apparent to one skilled in the art, that each branch of the dendritic polymer can be lengthened by any of a number of selected procedures. For example, each branch can be extended by multiple reactions with lysine molecules.

Erickson utilized the classic Merrifield technique in which a polypeptide of substantially any desired molecular weight is grown from a solid resin support. As the technique is utilized for the preparation of dendritic polymers, the linking molecule which joins the polymer to the resin support is trifunctional. One of the functional groups is involved in the linkage to the resin, the other two functional groups serve as the starting point for the growth of the polymer. The polymer is removed from the resin when the desired molecular weight has been obtained. One standard cleavage procedure is treatment with liquid hydrogen fluoride at 0° C. for one hour. Another, and more satisfactory procedure, is to utilize a complex of hydrogen fluoride and dimethylsulfide (HF:DMF) as described by Tam et al (1983). This procedure greatly minimizes side reactions and loss of peptide.

Denkewalter, in one example of his process, utilizes lysine as the core molecule. The amino groups of the core molecule are blocked by conversion to urethane groups. The carboxyl group is blocked by reaction with benzhydrylamine. Hydrolysis of the urethane groups generates a benzhydrylamide of lysine with two free amino groups which serve as the starting points for the growth of the dendritic polymer. This brief outline of three of the available procedures for producing dendritic polymers should be adequate to teach those skilled in the art the basic principles of the current technology. They will also teach the skilled artisan the salient features of the polymers, one of the most important of which is that the polymers provide a large number of available functional groups in a small molecular volume. The result is that a high concentration of antigens in a small volume can be achieved by joining the antigen to those available functional groups. Moreover, the resulting molecular product contains a high proportion of antigen on a relatively small carrier, i.e., the ratio of antigen to carrier is quite high. This is in contrast to conventional products used as a basis for vaccines. These conventional products often are composed of a small amount of antigen on a large amount of carrier.

Other important features of the dendritic polymer as an antigen carrier are that the exact structure is known; there are no contaminants which may be themselves antigenic, produce tissue irritation or other undesirable reactions; the exact concentration of the antigen is known; the antigen is symmetrically distributed on the carrier; and the carrier can be utilized as a base for more than one antigen so that multivalent vaccines can be produced. The principal advantage of MAPS as the basis for vaccines is that unlike other systems using natural carriers such as keyhole limpet hemocyanin, tetanus toxoid and bovine serum albumin, the dendritic polymers of MAPS as carriers are fully defined chemical entities on which the antigens are dispersed in known concentrations. Additionally, the antigen comprises a large part of the molecule, not a relatively small and undefined proportion of the molecule, as in the case of natural carriers.

When the MAPS is to be employed to produce a vaccine, also referred to herein as an immunizing composition, it is preferred that the core molecule be a naturally occurring amino acid such as lysine so that it can be dealt with by the body following the usual metabolic pathways. However, as will be explained more fully hereinafter, amino acids which are not naturally occurring, even those which are not α-amino acids can be employed. The acids, or any other asymmetric molecules used in building the core molecule can be in either the D or L form.

Although the dendritic polymers have been principally described hereinabove as polyamide polymers, it will be readily apparent that the carriers of this invention are not limited to dendritic polyamides. Any of a wide variety of molecules having at least two available functional groups can serve as core molecules. Propylene glycol, for example, can serve as the basis for a polyester dendritic polymer. Succinic acid with selected glycols or amines can serve as a core molecule to generate polyesters or polyamides. Diisocyanates can be used to generate polyurethanes. The important point is that the core molecule has at least two available functional groups from which identical branches can be generated by sequential scaffolding type reactions with additional molecules also having at least two available functional or anchoring groups on each branch. In the most simple case in which the core molecule has two available functional groups and each succeeding generation has two available functional groups, the number of anchoring sites to which antigen molecules can be anchored is expressed by $2^n$, where n is the number of the generation.

For a more complete discussion of the chemistry of dendritic polymers, attention is directed to Tomalia et al. (1985), Aharoni et al. (1982), and the following U.S. Pat. Nos. 4,289,872; 4,558,120; 4,376,861; 4,568,737; 4,507,466; 4,587,329; 4,515,920; 4,599,400; 4,517,122; and 4,600,535.

The antigenic product used in the immunizing composition of the present invention, in a presently preferred embodiment, provides a multiple antigen peptide system comprising a dendritic polymer base with a plurality of anchoring sites covalently bound to antigenic molecules which may be the same or different. The polymers comprise a central core molecule having at least two functional groups to which molecular branches having terminal functional groups are covalently bound. The terminal functional groups on the branches are covalently bonded to antigenic molecules, principally described herein as peptide antigens.

The selected antigen may be separately synthesized or otherwise obtained and joined to the carrier. Alternatively, the antigen may be synthesized on the carrier. For instance, if the antigen is an oligopeptide or relatively low molecular weight polypeptide, and the available functional groups on the polymer are amino groups or carboxyl groups, the antigen can be synthesized by extending each branch of the polymer utilizing known peptide synthesis techniques.

Figure 2B:
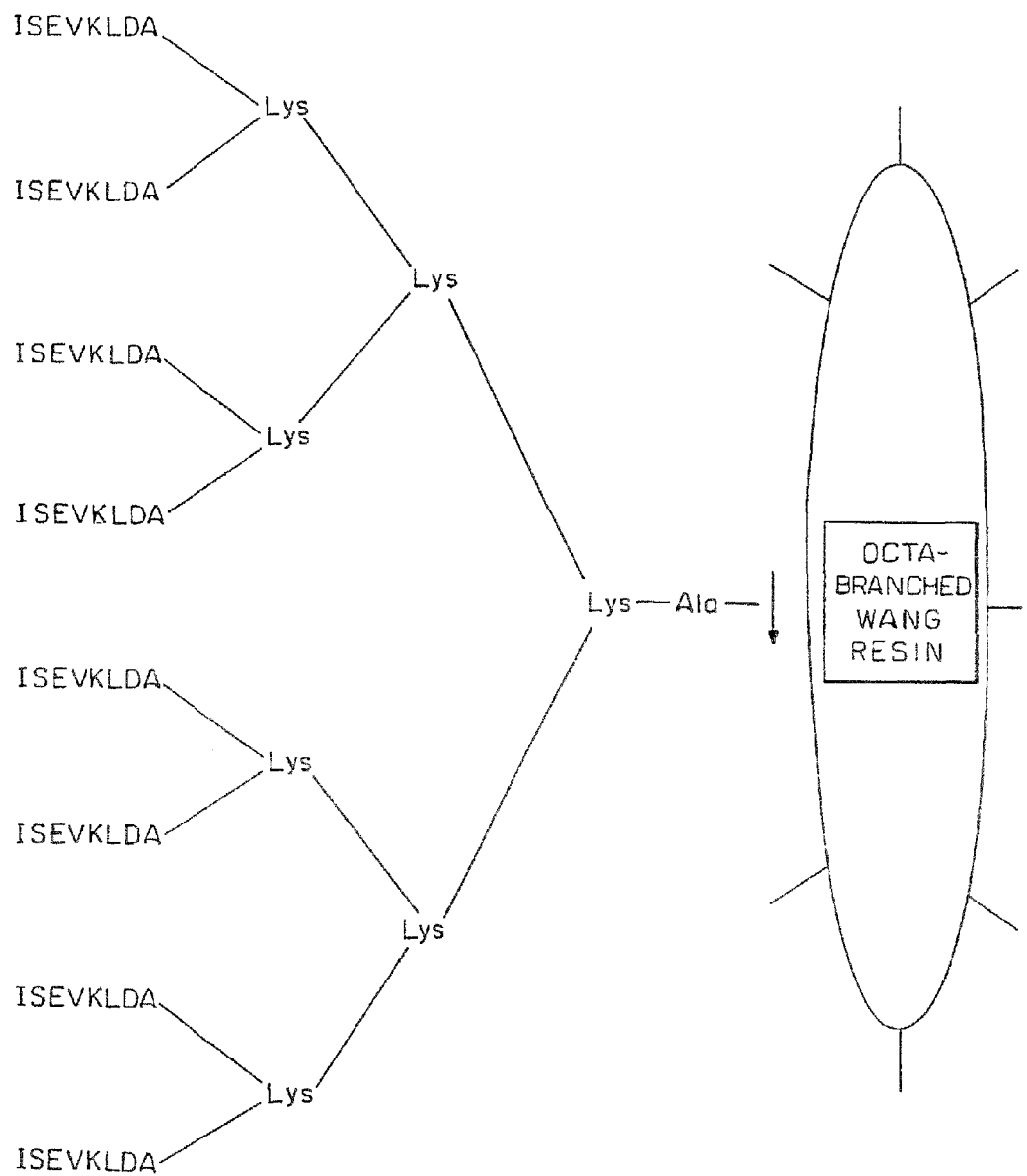
Figure 2C:
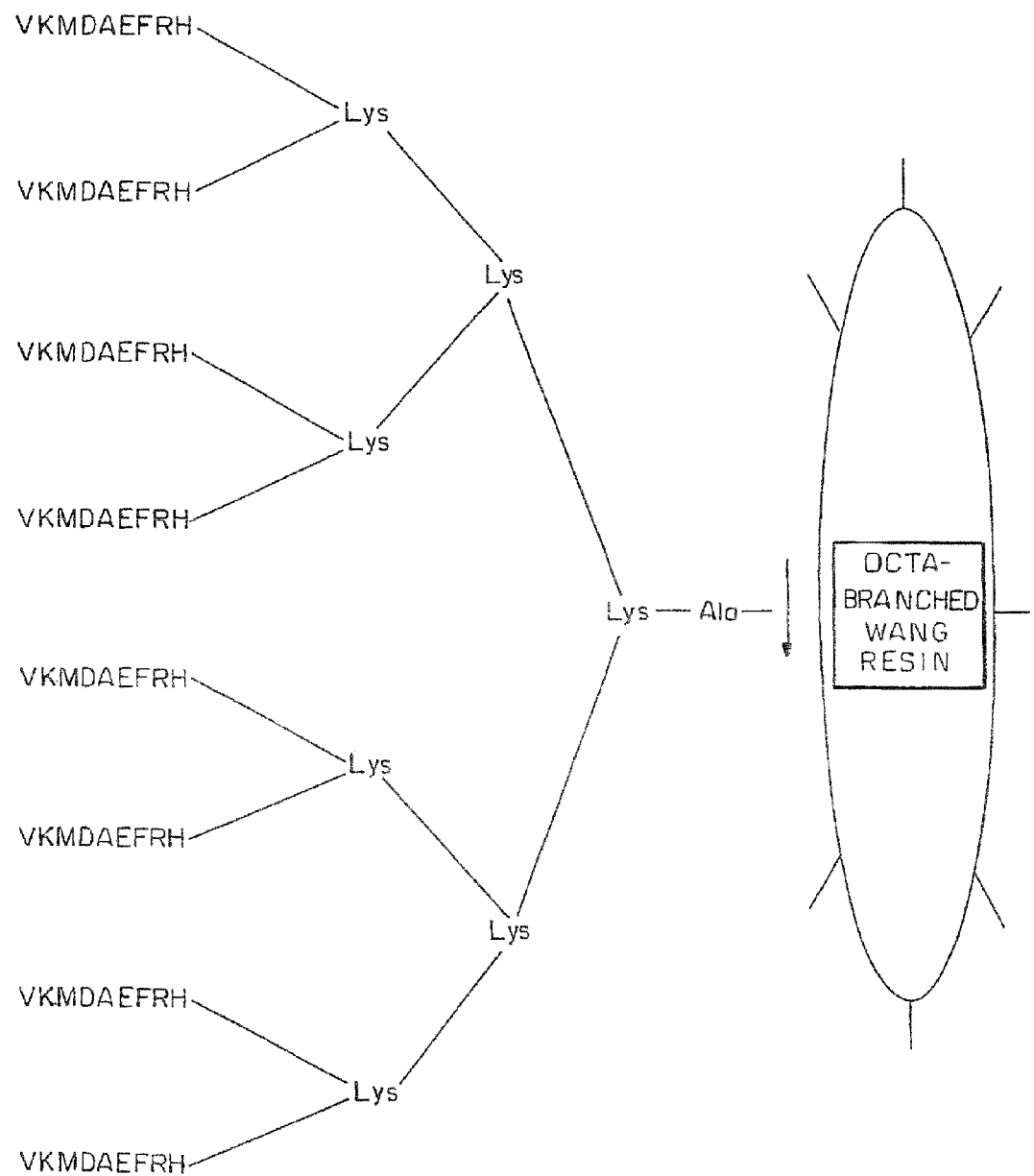

FIGS. 2A-2C shows the structures of three embodiments of MAP dendritic polymer on a resin which may be employed in the practice of the present invention. As can be seen, they are third generation dendritic polylysine products. It may be obtained commercially, for example, as an octa-branched or tetra-branched Wang resin with a MAP core from a number of suppliers, i.e., Advanced ChemTech, Inc. Louisville, Ky., or it may be produced by conventional solid phase techniques by generating the polymer on a Pam or a Pop resin. See Mitchell et al, (1978) and Tam et al, (1980). The polymer is then cleaved from the resin using, preferably HF:DMS. The dendritic polylysine, was built from an alanine linker originally joined to the resin. Other linkers such as glycine can be employed. Of course, the linker can be omitted, or a plurality of linker molecules can be utilized.

Peptide antigens having either residues 1-8 of SEQ ID NO:1 where residue 6 is Met (FIG. 2A), residues 1-8 of SEQ ID NO:1 where residue 6 is Leu (FIG. 2B), or SEQ ID NO:5 (FIG. 2C) joined directly to each of the available functional groups on each terminal lysine moiety are shown in FIGS. 2A-2C. In the case when the antigen is a relatively short peptide, e.g., 6 to 14 residues, it may be useful to extend the polylysine by a linker such as a simple tri- or tetrapeptide of glycine, alanine or beta-alanine. However, for antigenic peptides with more than 14 residues, the linker is normally unnecessary.

Preferably the peptide antigens attached to each of the available functional groups on the terminal moiety to form an octavalent MAP are as follows:

(MAP)-ISEVKMDA (residues 1-8 of SEQ ID NO:1 where residue 6 is Met) contains an epitope spanning the β-secretase cleavage site of AβPP in normal people; and (MAP)-ISEVKLDA (residues 1-8 of SEQ ID NO:1 where reside 6 is Leu) contains an epitope spanning the β-secretase cleavage site of AβPP in the Swedish mutation of AD.

The peptide antigens will be synthesized (growing from the C-terminus to the N-terminus) on, e.g., an octa-branched Wang Resin, resin-β-Ala-Lys-2Lys-4Lys-4 Fmoc, which is a MAP core resin. The octa-branched Wang resin can be obtained from the supplier, Advanced ChemTech, Inc., Louisville, MY (www.peptide.com) and has a cleavable part consisting of beta-alanine to which seven lysines, branched like a tree, are attached. The branches terminate at four lysines with two Emoc groups each for a total of eight Fmoc groups. The synthesis of MAP can be performed according to the supplier's instructions or according to any number of peptide synthesis protocols, such as disclosed in U.S. Pat. No. 5,229,490 and Tam et al. (1989).

A preferred embodiment of the present invention has been described for convenience, principally as applied to products built on lysine as the core molecule. In fact, lysine and lysine-like molecules such as ornithine, nor-lysine and amino alanine are preferred molecules for building the product of this invention because they are relatively easy to obtain, they are easy to work with, and they afford good yields. Such core molecules can be represented by the general formula:

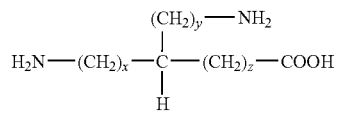

wherein x, y and z are integers from 0 to 10, preferably 0 to 4 provided that at least one of them is 1 and the amino groups cannot be attached to the same carbon atom. In the most preferred molecules, the total of x, y and z is from 2 to 6 and the amino groups are separated by at least two methylene groups.

Other preferred core molecules include ethylene diamine and like molecules with longer chains such as propylene diamine and butylene diamine. Such molecules may be represented by the general formula:

wherein n is an integer from 0 to 10, preferably 0 to 3. Of course ammonia can also be employed as a core molecule.

The development of synthetic vaccines against a large number of diseases has been greatly accelerated because of the recognition that a vaccine need not be based on a native protein, but may be based on a low molecular weight segment of the native protein. These segments, normally called immunogenic determinants or epitopes are capable of stimulating the production of antibodies which will protect against, e.g., infection by an infectious vector of the native protein antigen. The immunogenic determinants are often low molecular weight peptides which can be conveniently synthesized. If they cannot be synthesized, they may be separated in pure form from the native protein itself. Hereinafter, these antigenic immunostimulants will be referred to as antigenic peptides.

A principal embodiment used in the present invention may be broadly defined as an antigenic product comprising a dendritic core molecule or polymer to which a plurality of antigens such as antigenic peptides containing epitopes of the β-secretase cleavage site on AβPP are covalently bonded to the available functional groups. The antigens or epitopes may be different, although preferably the antigens or epitopes are the same.

More specifically, a principal embodiment used in the present invention may be defined as an antigenic product or a carrier system comprising a dendritic polymer base which is a central core molecule having at least two available functional groups to which branches of selected lengths are joined. Each branch of the molecule terminates with at least one available anchoring functional group, a plurality of which are covalently bonded to antigenic molecules.

The antigenic peptide that is covalently joined to the available terminal functional groups on the dendritic polymer contains at least one copy of an epitope spanning the β-secretase cleavage site of AβPP. When more than one copy of an epitope, such as two or three copies, is present on the antigenic peptide, a spacer of 2-8 amino acid residues, preferably 2-4 residues, separates the multiple copies of the epitope.

In a preferred embodiment used in the present invention, the epitope is ISEVKMDA or ISEVKLDA (residues 1-8 of SEQ ID NO:1). For small antigenic peptides, such as those having 6-12 residues, an octa-branched dendritic polymer (eight terminal functional groups) such as the octa-branched MAP Wang resin, is preferred. However, for larger peptides, in the range of about 20 amino acid residues or larger, a tetra-branched dendritic polymer, such as the tetra-branched MAP Wang resin is preferred.

An advantage of the dendritic polymer is that it can serve as a carrier for two or more different antigens, if desired. For instance, (MAP)-VKMDAEFRH (SEQ ID NO:5) represents a combination of the two different key epitopes of AβPP, the β-secretase Met-Asp cleavage site and the EFRH aggregating site of Aβ. One embodiment of the antigenic product used in the present invention is based on the use of a dendritic polylysine or other structurally similar molecule employing different amino blocking groups, one of which is stable to acid hydrolysis, the other of which is stable to alkaline hydrolysis. This makes it possible to protect either of the amino groups of lysine by the orthogonal protection method.

Fluorenylmethyloxycarbonyl (Fmoc) is a base labile protecting group and is completely stable to acidic deprotection. The t-butoxycarbonyl blocking group (Boc) is stable under basic conditions but not stable under mildly acidic conditions such as 50% trifluoroacetic acid. By choosing Boc-lys (Boc)-OH, Boc-lys (Fmoc)-OH, Fmoc-lys (Boc)-OH or Fmoc-lys (Fmoc)-OH, it is possible to place one set of antigens on the alpha amino group of lysine and another on the omega amino group. Those skilled in the art of peptide synthesis can readily devise methods of achieving the same types of products using diverse blocking groups and other dendritic polymers.

A few general observations applicable to the synthesis of MAPS will be of assistance to those skilled in the art. These are:

1. The syntheses generally require a long coupling time (2-4 hours).
2. Dimethyl formamide is generally a more suitable solvent than methylene dichloride.
3. The peptide resin should not be dried at any stage of the synthesis since resolution is extremely difficult.
4. Coupling should be closely monitored for completion of the coupling by the quantitative ninhydrin method.
5. The MAPS is best cleaved from the resin by the improved acid deprotection method with either HF or TFMSA (Tam, et al., 1983 and 1986) in dimethyl sulfide to avoid strong acid catalyzed side reactions.
6. MAPS tend to strongly aggregate after cleavage from the resin support. Purification is best effected by extensive dialysis under basic and strongly denaturing conditions in a dialysis medium which is 8M in urea and mercaptoethanol to remove undesirable aromatic additives of the cleavage reactions such as p-cresol and thiocresol. Further purification, if desired, can be effected using high performance gel-permeation or ion exchange chromatography. In most cases the MAPS could be used directly without further purification.

It will be apparent to those skilled in the art that many variations of the structures shown and discussed herein are possible. All such variations are specifically included within the scope of this invention. For example, see U.S. Pat. No. 5,229,490, the entire content of which is incorporated herein by reference.

The antigenic product used in the present invention may include a lipophilic membrane anchoring moiety that confers adjuvant properties among its advantages. A lipophilic membrane-anchoring moiety at the carboxyl terminus of MAP enables further non-covalent amplification by a liposome or micellar form. Accordingly, the immunizing composition of the present invention, which contains the antigenic product, may further be prepared with a variety of vehicles, including encapsulation within liposomes, for greater efficiency of delivery and concomitantly reduced dosage. The preparation of liposomes is well known in the art.

Tripalmitoyl-S-glyceryl cysteine (P3C) and palmitoyl lysine (PL) are non-limiting examples of suitable lipophilic moieties for the antigenic product used in the present invention. P3C, which is a lipoamino acid from *Escherichia coli*, is a B cell mitogen that has proved particularly successful as a non-toxic adjuvant. See U.S. Pat. No. 5,580,563 and DeFoort et al., (1992), the entire contents of which are incorporated herein by reference.

Because the MAPs used in this invention as an antigenic product provides a high concentration of antigen in a small molecular volume, in many instances the vaccine/immunizing composition of the invention may be employed, without adjuvants. However, if an adjuvant is employed, it may be selected from any of those normally employed to stimulate the immunogenic systems of mammals.

As used herein the term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The viral display vehicle as an antigenic product used in the immunizing composition according to the present can be a double stranded DNA virus, a single stranded DNA virus, an RNA virus (positive or negative strand). Preferably, the display vehicle is a filamentous bacteriophage such as fd, f88, f1, and M13. Due to its linear structure, filamentous phage has high permeability to different kinds of membranes (Scott et al., 1990) and following the olfactory tract, it reaches the hippocampus area via the limbic system to target affected sites. The treatment of filamentous phage with chloroform changes the linear structure to a circular one, which prevents delivery of phage to the brain.

While the fd filamentous phage is a particularly preferred phage sequence for use in the present invention, it should be understood that all filamentous phages are very similar and have the same gene organization (Model et al, 1988). Thus, the principles of the present invention can be applied to any of the filamentous phages, such as M13, f1 and others.

Preferably, the display vehicle is capable of propagation in the recipient. Thus, for example, a bacteriophage display vehicle can be propagated in bacterial flora, such as *Escherichia coli* residing in the recipient's body. Alternatively, the display vehicle can be an in vivo non-propagateable particle. Although concerns about the potential infection of the natural intestinal flora (Delmastro et al., 1997; Willis et al., 1993; and Poul et al., 1999) have been expressed, UV inactivation of phage showed (Delmastro et al., 1997) that they are as immunogenic as their infective counterparts. Use of inactivated phage may preclude incorporation of phage encoded transgenes into the nucleus for subsequent expression in host cells (Larocca et al., 1998), an important practical consideration. Therefore, according to alternate preferred embodiments, the display vehicles employed in the present invention may be either replicating or non-replicating.

Phage or virus display involves the expression of cDNA clones as fusion proteins with phage or virus coat proteins. If the cDNAs selected for expression encode antigens, the phage or virus may then be employed as an antigen presenting vehicle, which can optionally replicate within a recipient.

Antigens displayed by a phage or virus may be used directly for vaccination, without antigen purification. In this case, the bulk of the coat proteins serve to stimulate a general immune response because they are "non-self" with respect to the vaccinated subject. The antigen-coat protein fusion elicits a specific antibody against epitopes in the displayed cDNA gene product.

According to a preferred embodiment of the antigenic product used in the immunizing composition according to present invention, the display vehicle is selected such that less than 30 days following an introduction of a triple dose of $10^{10}$ units thereof to the recipient, a titer of the antibodies in the recipient is above 1:50,000, as is determined by ELISA.

The vaccines/immunizing composition of the invention may be defined as comprising a pharmaceutically acceptable carrier, excipient, adjuvant, or auxiliary agent, together with an amount of antigenic product of the invention which is sufficient to produce an immunological response. An effective amount may be very small. It will, as is known, vary with the antigen. With the MAPS antigenic product of this invention, because of the high concentration of antigen in a low molecular volume, it will be lower than with ordinary vaccines employing the same antigens. The quantity which constitutes an effective amount may vary depending on whether the vaccine is intended as a first treatment or as a booster treatment.

It may be convenient to provide the products of this invention as lyophilized or freeze dried powders ready to be reconstituted with a pharmaceutically acceptable carrier just prior to use.

In prophylactic applications, the immunizing composition of the present invention is administered to a subject/patient susceptible to, or otherwise at risk of Alzheimer's disease, in an amount sufficient to the onset of the disease, including biochemical, histologic and/or behavioral symptoms of the disease, its complications and intermediate pathological phenotypes presenting during development of the disease. Individuals who have a known genetic risk of Alzheimer's disease include those having relatives who have experienced this disease and those whose risk is determined by analysis of genetic or biochemical markers. Genetic markers of risk towards Alzheimer's disease include mutations in the APP gene, particularly mutations at positions 717 and positions 670 and 671, referred to as the Hardy and Swedish mutations, respectively. In therapeutic applications, the immunizing composition of the invention is administered to a patient suspected of, or already suffering from Alzheimer's disease in an amount sufficient to at least partially arrest the symptoms of Alzheimer's disease (biochemical, histologic and/or behavioral), including its complications and intermediate pathological phenotypes in development of Alzheimer's disease. An amount adequate to block β-secretase cleavage of AβPP and inhibit formation of Aβ is defined as an effective dosage. In the method for inducing an immune response against the β-secretase cleavage site of AβPP, the immunizing composition of the present invention is usually administered in several doses until a sufficient immune response has been achieved. Typically, the immune response is monitored and repeated doses are given if the immune response starts to wane.

Effective dosages of the immunizing composition of the present invention for inducing an immune response against the β-secretase cleavage site of AβPP vary depending upon many different factors, including means of administration, target site, physiological state of the patient, whether the patient is human or an animal, other medications administered, and whether treatment is prophylactic or therapeutic. Usually, the patient is a human, but nonhuman mammals including transgenic mammals can also be treated. Treatment dosages need to be titrated to optimize safety and efficacy. The amount of immunogen depends on whether adjuvant is also administered, with higher dosages more likely to be required in the absence of adjuvant. The 1-500 μg per patient and more usually from 5-500 μg per injection is used for human administration. Occasionally, a higher dosage of 1-2 mg per injection is used. Typically about 10, 20, 50 or 100 μg is used for each human injection. The mass of immunogen also depends on the mass ratio of immunogenic epitope within the immunogen to the mass of immunogen as a whole. The timing of injections can vary significantly from once a day, to once a year, to once a decade. On any given day that a dose of immunogen is given, the dosage is greater than 1 μg/patient and usually greater than 10 μg/patient if adjuvant is also administered, and may be greater than 10-100 μg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

The immunizing composition of the present invention for inducing/eliciting an immune response can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is mostly typically performed in the arm or leg muscles.

The immunizing composition of the invention can sometimes be administered in combination with an adjuvant. A variety of adjuvants can be used in combination with the antigenic product of the invention to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211, RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., 1995); U.S. Pat. No. 5,057,540 (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., 1997). Another adjuvant is CpG (WO 98/40100). Alternatively, the antigenic product can be coupled to an adjuvant. However, such coupling should not substantially change the conformation of the epitope so as to affect the nature of the immune response thereto. Adjuvants can be administered as a component of an immunizing composition with the antigenic product of the invention administered separately, before, concurrently with, or after administration of the adjuvant.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutarninyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS) (Ribi ImmunoChem, Hamilton, Mont.) containing 2% squalene, 0.2% Tween 80, and one or more bacterial cell wall components from the group consisting of 5 monophosphoryllipid A (MPL), tiehalose dimycolate (TDM), and cell wall skeleton (CWS), preferably MPL+CWS (Detox™). Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include Complete Freunds Adjuvant (CFA), Incomplete Freunds Adjuvant (IFA) and cytokines, such as interleukins (IL-1, IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., 1998), optionally in combination with any of in QS-2, and WPL and all combinations thereof.

The antigenic product of the present invention is often administered as pharmaceutical compositions comprising an active agent, i.e., the antigenic product, and a variety of other pharmaceutically acceptable components. See Remington's Pharmaceutical Science (15$^{th}$ ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or auxiliary agents or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, the antigenic product of the present invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, 1990 and Hanes, 1997).

Patients amenable to treatment include individuals at risk of Alzheimer's disease but not showing symptoms, as well as patients presently showing symptoms. Virtually anyone is at risk of suffering from Alzheimer's disease if he or she lives long enough. Therefore, the present antigenic product can be administered prophylactically to the general population without the need for any assessment of the risk of the subject patient. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and the Swedish familial AD mutations, respectively. Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or B-cell responses to the antigenic product of the present invention over time. If the response falls, a booster dosage is indicated. In the case of potential Down's syndrome patients, treatment can begin antenatally by administering therapeutic agent to the mother or shortly after birth.

The present invention also provides for methods of detecting an immune response against the β-secretase cleavage site of AβPP in a patient suffering from or susceptible to Alzheimer's disease. The methods are particularly useful for monitoring a course of treatment being administered to a patient. The methods can be used to monitor both therapeutic treatment on symptomatic patients and prophylactic treatment on asymptomatic patients by monitoring antibody produced in response to administration of immunogen.

Some methods entail determining a baseline value of an immune response in a patient before administering a dosage of the antigenic product, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an immunogenic agent are expected to show an increase in immune response with successive dosages, which eventually reaches a plateau. Administration of agent is generally continued while the immune response is increasing. Attainment of the plateau is an indicator that administration of the immunogen can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering the antigenic product are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values is an indicator that the administration of treatment can be discontinued or reduced in dosage or frequency.

In other methods, a control value of immune response (e.g., a mean and standard deviation) is determined from a control population of individuals who have undergone treatment with the antigenic product and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous or cerebrospinal fluid from the patient. The sample is analyzed for indication of an immune response to the antigenic product. The immune response can be determined from the presence of antibodies that specifically bind to the β-secretase cleavage site of AβPP, i.e., ELISA.

A further aspect of the present invention provides for antibodies raised against the AβPP epitope spanning the β-secretase cleavage site of AβPP as carried on the antigenic product in the immunizing composition according to the present invention and for molecules that includes the antigen-binding portion of such antibodies.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')2 fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked VH-VL or single-chain FV). Both VH and VL may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the VH and VL chains are known, may be accomplished in accordance with the methods described, for example, in U.S. Pat. Nos. 4,946,778, 5,091,513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mabs) are a substantially homogeneous population of antibodies to specific antigens. MAbs may be obtained by methods known to those skilled in the art. See, for example Kohler et al, (1975); U.S. Pat. No. 4,376,110; Harlow et al, (1988); and Colligan et al, (2001), the entire contents of which references are incorporated entirely herein by reference. Such antibodies may be of any immunoglobulin class including IgG, IgM, IgE, IgA, and any subclass thereof. The hybridoma producing the mabs of this invention may be cultivated in vitro or in vivo. High titers of mabs can be obtained by in vivo production where cells from the individual hybridomas are injected intraperitoneally into pristane-primed Balb/c mice to produce ascites fluid containing high concentrations of the desired mabs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mabs are used. Chimeric and humanized antibodies and methods for their production are well-known in the art, such as Cabilly et al (1984), Morrison et al (1984), Boulianne et al (1984), Cabilly et al, European Patent 0 125 023 (1984), Neuberger et al (1985), Taniguchi et al, European Patent 0 171 496 (1985), Morrison et al, European Patent 0 173 494 (1986), Neuberger et al, WO 8601533 (1986), Kudo et al, European Patent 0 184 187 (1986), Sahagan et al (1986); Robinson et al, WO 9702671 (1987), Liu et al (1987), Sun et al (1987), Better et al (1988), and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

An increasing body of evidence shows that olfactory deficits and degenerative changes in the central olfactory pathways are affected early in the clinical course of AD. Moreover, the anatomic patterns involved in AD suggest that the olfactory pathway may be the initial stage in the development of AD.

Olfactory receptor neurons are bipolar cells that reside in the epithelial lining of the nasal cavity. Their axons traverse the cribriform plate and project to the first synapse of the olfactory pathway in the olfactory bulb of the brain. The axons of olfactory neurons from the nasal epithelium form bundles of 1000 amyelinic fibers. This configuration makes them a highway by which viruses or other transported substances may gain access to the CNS across the BBB.

In the early stages of AD, the BBB may limit the entry of antibody circulating in the periphery to the CNS. In contrast, single chain antibodies or molecules having an antigen-binding portion of an antibody directed against an epitope spanning the β-secretase cleavage site of AβPP, which antibodies or molecules are displayed on a phage surface have the potential not only be delivered directly to the CNS by intranasal administration but also to prevent olfactory permanent damage by Aβ in the patients. As previously shown, intranasal administration (Mathison et al., 1998; Chou et al., 1997 and Draghia et al., 1995) enables the direct entry of viruses and macromolecules into the CSF or CNS.

Use of olfactory receptor neurons as a point of delivery for an adenovirus vector to the brain is reported in the literature. This method reportedly causes expression of a reporter gene in the brain for 12 days without apparent toxicity (Draghia et al., 1995).

Thus, according to the method for passive immunization according to the present invention, a vehicle displaying an immunological antigen-binding portion of an antibody capable of blocking the β-secretase cleavage site of AβPP is delivered via this route to the brain.

As Aβ is produced continuously by cells in peripheral tissues which cross the blood brain barrier (BBB) leading to localized toxic effects in specific neuronal populations, intranasal administration of such a vehicle may also prevent the progression of the disease by minimizing the amount of peripheral Aβ available to form plaques.

Antibody phage or virus display is accomplished, for example, by fusing the coding sequence of the antibody variable regions to a phage or virus coat protein. To this end, the variable (V) regions ($V_H$ and $V_L$) mRNA isolated from antibody-producing cells is reverse-transcribed into cDNA, and heavy and light chains assembled randomly to encode single chain Fv (scFv). These cassettes are cloned directly into a suitable vector such as a phagemid vector for expression and display on the phage or virus surface. This linkage between antibody genotype and phenotype allows the enrichment of antigen specific phage or virus antibodies, using immobilized or labeled antigen. Phage or virus that display a relevant antibody will be retained on a surface coated with antigen, while non-adherent phages or viruses will be washed away. Bound phages or viruses can be recovered from the surface, re-infected into suitable host cells and re-grown for further enrichment and, eventually for binding analysis.

The success of antibody phage or virus display hinges on the combination of this display and enrichment method. Phage or virus antibody genes can be sequenced, mutated and screened to improve antigen binding.

It is possible to rearrange the genes which code for the various regions of an antibody molecule such that its specificity and affinity for an antigen are altered. The antibody can be maintained on the surface of the phage or virus for further manipulation or be released as soluble scFv (~25 kDa) fragment.

Since its invention at the beginning of the 1990's, antibody phage display has revolutionized the generation of monoclonal antibodies and their engineering. This is because phage display allows antibodies to be made completely in vitro, bypassing the immune system and the immunization procedure, and allowing in vitro tailoring of the affinity and specificity of the antibody. It is therefore anticipated that the most efficient new vaccine development strategies will employ this technology.

Additional features can be added to the vector to ensure its safety and/or enhance its therapeutic efficacy. Such features include, for example, markers that can be used to negatively select against cells infected with the recombinant virus such as antibiotic sensitivity. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell.

The direct brain delivery of antibodies overcomes crossing the BBB by using olfactory neurons as transporters to the brain. In the olfactory epithelium, the dendrites of the primary olfactory neurons are in contact with the nasal lumen, and via the axons, these neurons are also connected to the olfactory bulbs of the brain. Phages that come into contact with the olfactory epithelium can be taken up in the primary olfactory neurons and be transported to the olfactory bulbs, and even further into other areas of the brain.

A further aspect of the present invention provides a pharmaceutical composition containing a pharmaceutically acceptable carrier, excipient, diluent, or auxiliary agent and the viral display vehicle displaying on its surface a single chain antibody directed against an epitope spanning the β-secretase cleavage site of AβPP.

Having now generally described the invention, the same will be more readily understood through reference to the following example which is provided by way of illustration and is not intended to be limiting of the present invention.

EXAMPLE

Materials and Results

Figure 3:
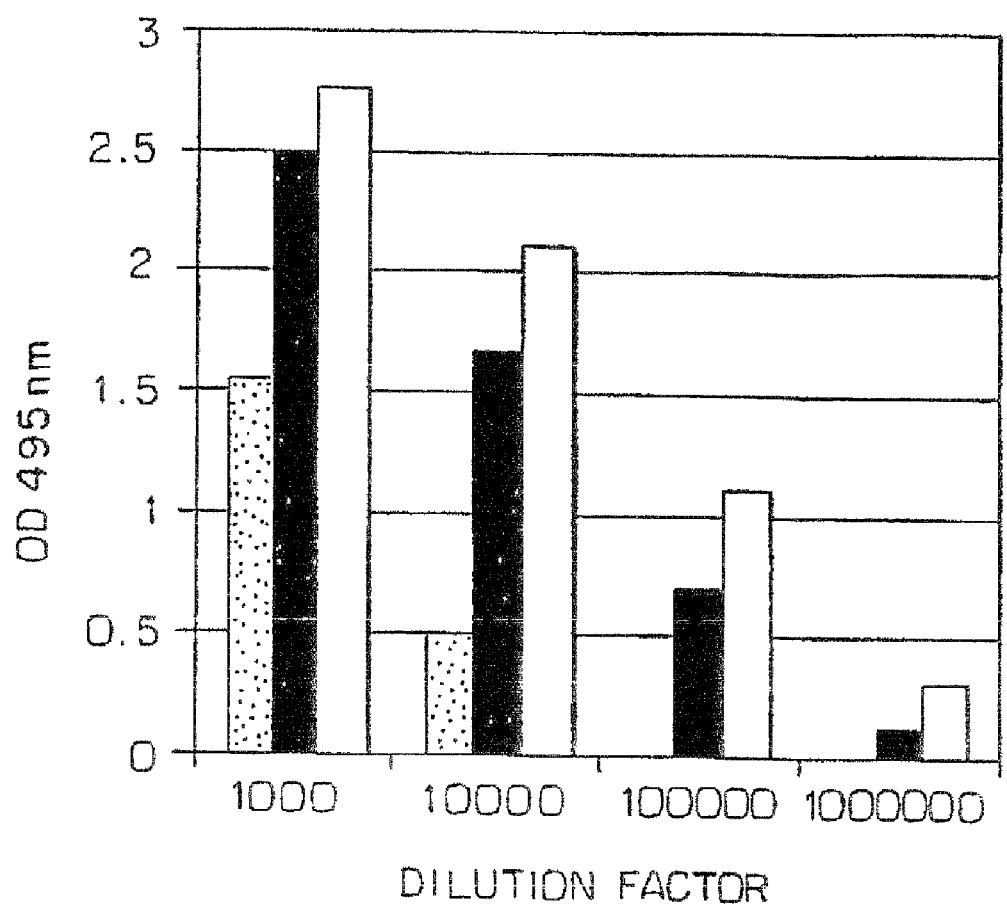
FIG. 3 is a graph showing the immune response after immunization with MAP-ISEVKLDA (residues 1-8 of SEQ ID NO:1, where residue 6 is Leu).
Figure 3:
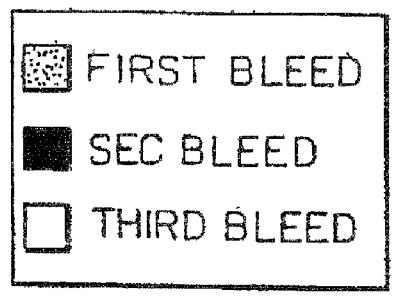

Immunization:

3 groups of Balb/c mice were injected with 3 different MAP (octa-branched) conjugated peptides:

ISEVKMMDA (residues 1-8 of SEQ ID NO:1, where residue 6 is Met), VKMDAEFRH (SEQ ID NO:5) and ISEVKLDA (residues 1-8 of SEQ ID NO:1, where residue 6 is Leu). The stock solution (2 mg/ml) was prepared as follows: 1000 µl of double distilled water (DDW), 665 µl of Freund's adjuvant (Complete Freund's adjuvant on first injection and Incomplete Freund's adjuvant on subsequent injections) and 335 µl of peptide stock solution. 300 µl of the vaccination solution (immunizing composition) was injected into each mouse every two weeks after initial injection. The highest immune response raised against MAP-ISEVKLDA (residues 1-8 of SEQ ID NO:1, where residue 6 is Leu) is shown in FIG. 3.

ELISA Procedure for IgG Titer Quantification:

96-well ELISA plates were coated with 50 µl/well peptide stock solution at dilution of 1:500 in coating buffer (0.1M $Na_2CO_3$, pH 9.6) and incubated overnight at 4° C. The plates were washed with 2×PBS (0.05% TWEEN) and 2×PBS, blocked with 3% milk/PBS 180 µl/well and incubated for 1.5 hr at 37° C. Serum dilutions in 1% milk/PBS 50 µl/well were incubated for 1 hr at 37° C., then washed again with 50 µl/well α-mouse-IgG (H+L)HRP conjugated with dilution of 1:5000 in 1% milk/PBS incubated for 1 hr at 37° C. Additional washings contained PBS (0.05% TWEEN) and finally PBS. Reaction was done with 50 µl/well of 15 ml 0.05M citrate buffer with 30 mg OPD and 5 µl of 30% $H_2O_2$. Reaction time was 5-10 minutes and was then stopped by addition of 25 µl/well 4 M HCl.

Cell Line:

Cell Culture-Chinese hamster ovary (CHO) cells were grown in Dulbecco's modified Eagle's medium (F-12) containing 10% fetal calf serum (FCS) and 2.5 mM L-glutamine. Stably transfected CHO cell lines expressing wild type AβPP 751 were generated with expression vector pCMV751 using Lipofectin-mediated transfection (Life Technologies, Inc., Gaithersburg, Md.) and selected by G418 resistance. A 6-well plate was then seeded with $2.5 \times 10^6$ to $4 \times 10^6$ cells from each transfected cell line. Following overnight incubation, serum-free medium was added to each well and then the cells were incubated in a solution of anti-β-secretase cleavage site on AβPP serum and non-injected mouse serum as control, then incubated for 48 h. Media were collected from each well and subjected to ELISA.

Figure 4:
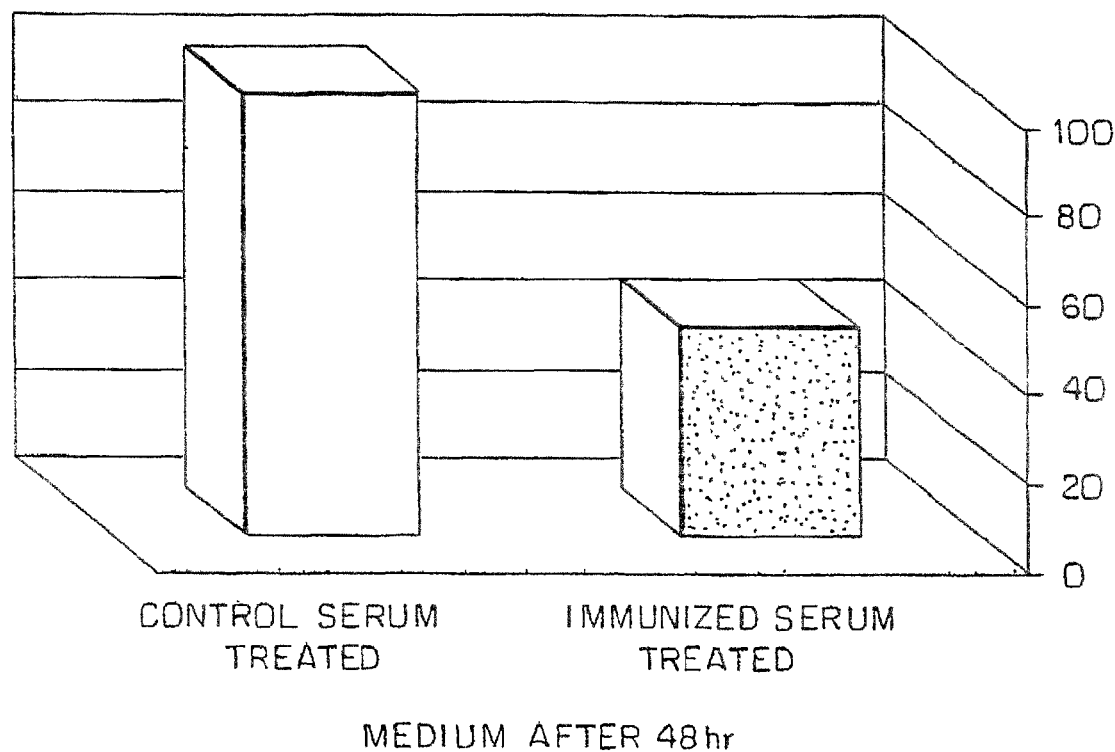
FIG. 4 is a graph showing the inhibition of total amyloid beta peptide (Aβ) secretion to growth media after 48 hrs. as measured by ELISA.

Two Site-sandwich Aβ ELISA:

A two site-sandwich ELISA was used to measure Aβ production and secretion from the above serum-treated and untreated cells. The monoclonal anti-Aβ antibody 266 was used as a capture antibody. Ninety-six well plates were coated with a solution of 266 (0.1 µg/well) and 0.1M carbonate buffer (0.1M $Na_2CO_3$, pH 9.6), and incubated overnight at 4° C. The plates were washed with 2×PBSt (0.05% TWEEN) and 2×PBS, subsequently blocked with 180 µl/wall 3% BSA/PBS and incubated for 2.5 hr at 37° C., then washed as above. Biotinylated monoclonal anti-Aβ antibody 6C6 (125 ng/well) for total Aβ and biotinylated monoclonal anti-Aβ1-42 antibody 8G7 (25 ng/well) for Aβ1-42 specific, both in 1% BSA/PBS, were used for detection. Plates were washed and avidin-conjugated alkaline phosphatase (Sigma, St. Louis, Mo.) (1 µg/well) was added for 2 hr at room temperature, then they were washed in 3×PBSt (0.05% TWEEN) and 4×PBS. The substrate p-nitrophenylphosphate (PnPP; Sigma) was used as the reporter system. Reaction was done with 50 µl/well (15 ml) of diethanolamine buffer with 30 mg PnPP. PnPP fluorescence was examined at wavelength of 405 nm. For construction of standard curves the Aβ standard (1-28) and Aβ standard (1-42) were prepared in the presence of protease inhibitors and 1% BSA in serum-free medium or extraction buffer (FIG. 4). FIG. 4 shows the inhibition of total amyloid beta peptide (Aβ) secretion to growing media as measured by ELISA.

Quantification of Intracellular Aβ (1-42)

Figure 5:
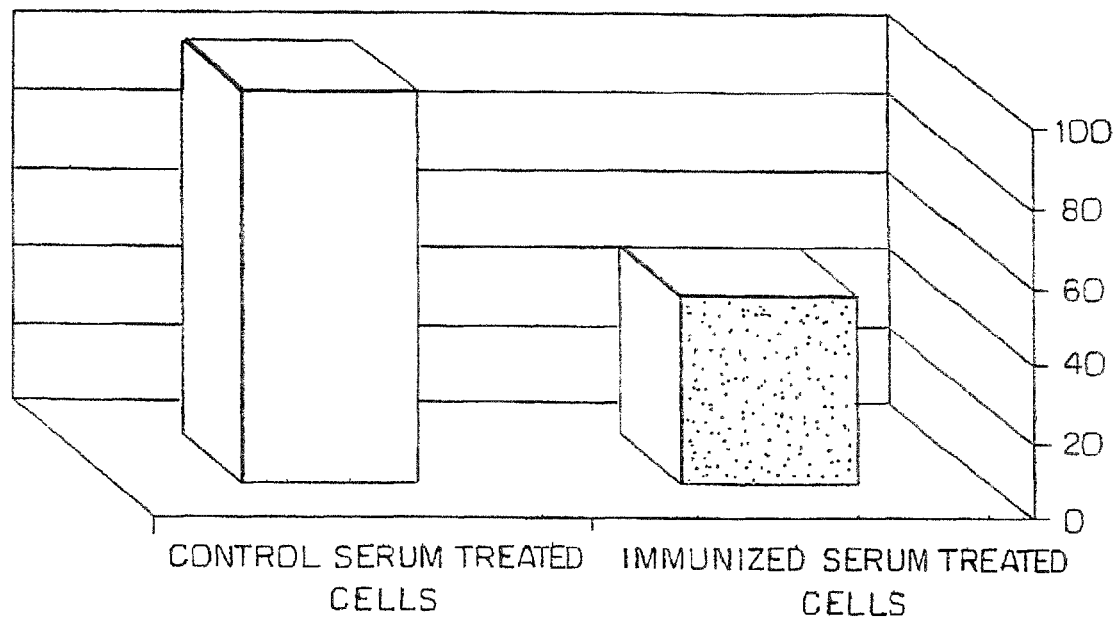
FIG. 5 is a graph showing the inhibition of intracellular accumulation of Aβ 1-42 peptide after 5 days incubation as measured by ELISA.

CHO cells were collected from each well using cell scraper in their growing media. The collected media were centrifuged at 3000 g for 2 min, collected cells were washed with PBS and centrifuged twice. Cells were suspended in 100 µl 70% formic acid and sonicated for 10 sec with probe sonicator. The solution was centrifuged at 100,000 g for 20 min at 4° C. to remove insoluble material; supernatant was neutralized with 1.9 ml 1M TRIS. Samples of this solution were diluted 1:3 in $H_2O$ and 300 µl of it was added for the ELISA, as described above. After only 5 days incubation, considerable inhibition of Aβ (1-42) accumulation, as measured by ELISA, was found (FIG. 5).

Figure 6:
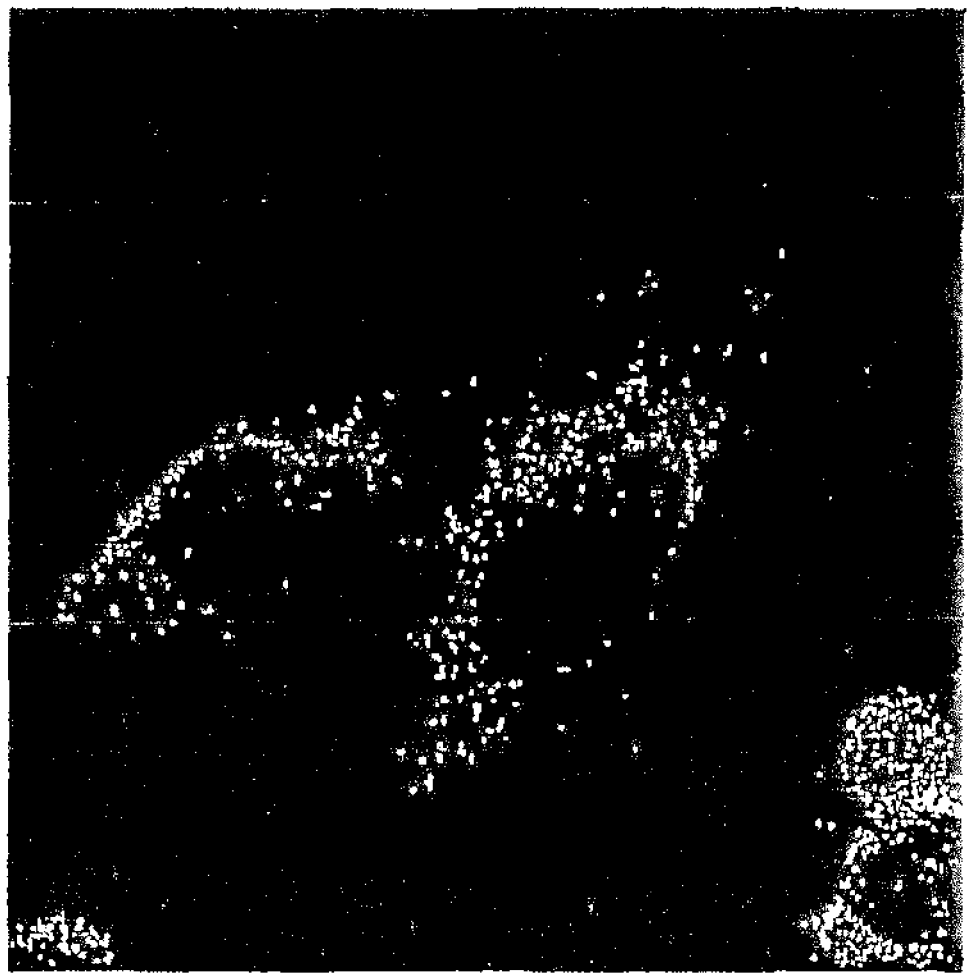
FIG. 6 is a confocal microscopy image showing co-localization in the perinuclear region of anti-β secretase cleavage site antibodies according to the present invention and BACE antibodies raised against the β-secretase enzyme itself.

Confocal Microscopy for Co-localization of AβPP-Sera Antibody Complex with BACE (β-secretase) into the Cells:

CHO cells overexpressing AβPP 751 were grown for 24 hr in 6-wells plates, washed with 3×PBS and fixed with 4% (in PBS) paraformaldehyde for 30 min at room temperature. Cells were washed as above and permeabilized by adding 0.3% TRITON-100 in 1% BSA/PBS for 5 min, then washed with 0.5% 3×(BSA/PBS). Non-specific binding with rabbit serum 1:150 for 2 hr was followed by washing as described above. Anti-β secretase cleavage site on AβPP serum or α-BACE1 (raised against the β-secretase enzyme itself and supplied by Calbiochem, San Diego, Calif.), in dilution of 1:2000, was added, followed by incubation for 2 hr, washed as described above and subjected to secondary antibody, as follows: α-mouse-Cy3 for anti-β secretase site on AβPP serum and/or α-rabbit-FITC for α-BACE1. In FIG. 6, confocal microscopy of anti-β secretase cleavage site on AβPP antibodies and BACE antibodies showed co-localization (light spots) in the cell perinuclear region.

Immunfluorescence Microscopy for Internalization Assay of Antibodies Against β-Secretase Cleavage Site:

CHO cells overexpressing AβPP 751 were grown for 24 hr in 6-well plates. After washing, new media containing anti-β secretase cleavage site on AβPP serum in dilution of 1:500 were added. Cells were incubated for 30 min and then washed with 3×PBS and fixed with 4% (in PBS) paraformaldehyde for 30 min at room temperature. Cells were washed as above and divided into permeabilized cells by adding 0.3% TRITON-100 in 1% BSA/PBS and incubated for 5 min. As control, untreated cells were washed with 0.5% 3× (BSA/PBS).

Figure 7A:
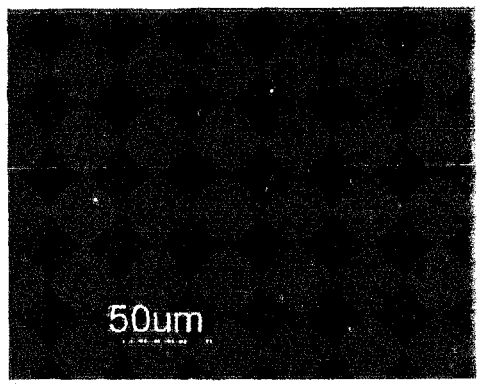
FIGS. 7A and 7B are images of permeabilized (FIG. 7A) and control (FIG. 7B) cells immunostained with anti-β secretase cleavage site on APP antibody and a secondary antibody.
Figure 7B:
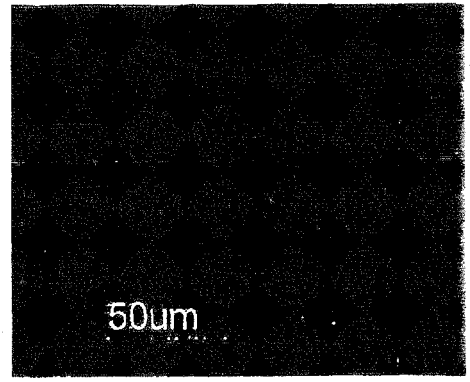

The blocking step was done with 3% BSA for 2 hr followed by washing step as above. Secondary antibody was incubated for 1 hr at room temperature in the dark, after which it was washed with 3×PBS and mounted with ProLong anti-fade kit (Molecular Probes, Eugene, Oreg.). FIG. 7A shows the immunostaining of internalized anti-β-secretase cleavage site AβPP antibody after fixation and permeabilization. FIG. 7B is the control.

Figure 8:
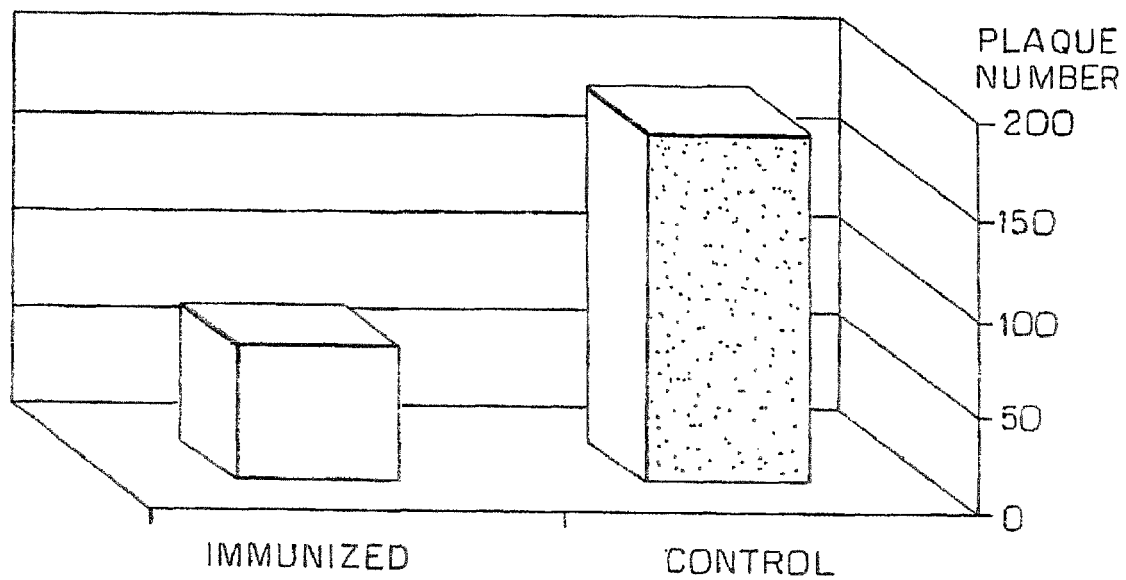
FIG. 8 is a graph showing reduction of plaque number in transgenic mice immunized with the antigen, compared with untreated mice.

Inhibition of Plaque Formation in AβPP Transgenic Mice:

6 mice were immunized as describe above and 3 mice were used as control. After five months of immunization, the mice were sacrificed and brain slices were subjected for standard ThS protocol plaque staining. Plaque number was counted under microscope examination and a reduction of plaque number in transgenic mice immunized with the antigen, compared to untreated mice, was observed (FIG. 8).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Banks et al., "Bidirectional passage of peptides across the blood-brain barrier", *Prog Brain Res.* 91:139-148 (1992)

Better et al, "*Escherichia coli* secretion of an active chimeric antibody fragment", *Science* 240:1041-1043 (1988)

Bluthner et al, "Mapping of epitopes recognized by PM/Sc1 autoantibodies with gene-fragment phage display libraries", *J Immunol Methods* 198:187-198 (1996)

Bobo et al., "Convection-enhanced delivery of macromolecules in the brain", *Proc. Natl. Acad. Sci. U.S.A.*, 91:2076-2080 (1994)

Bonnycastle et al., "Probing the basis of antibody reactivity with a panel of constrained peptide libraries displayed by filamentous phage. *J Mol Biol.*, 24;258(5):747-62 (1996)

Broadwell, "Transcytosis of macromolecules through the blood-brain barrier: a cell biological perspective and critical appraisal", *Acta Neuropathol.*, 79: 117-128 (1989)

Cabilly et al, "Generation of antibody activity from immunoglobulin polypeptide chains produced in *Escherichia coli*." *Proc Natl Acad Sci USA* 81:3273-3277 (1984)

Chang et al., *Advanced Drug Delivery Reviews*, 32:173-186 (1998)

Colligan et al, *Current Protocols in Immunology*, Green Publishing Assoc., and Wiley Interscience, New York (2001)

Cortese et al, "Epitope discovery using peptide libraries displayed on phage", *Trends Biotechnol* 12:262-267 (1994)

Cortese et al, "Identification of biologically active peptides using random libraries displayed on phage", *Curr Opin Biotechnol* 6:73-80 (1995)

Cortese et al, "Selection of biologically active peptides by phage display of random peptide libraries. *Curr Opin Biotechnol* 7:616-621 (1996)

Cwirla et al, "Peptides on phage: a vast library of peptides for identifying ligands", *Proc Natl Acad Sci USA* 87:6378-6382 (1990)

DeFoort et al., *Int. J. Peptide Protein Res.*, 40:214-221 (1992)

Dotto et al, "The functional origin of bacteriophage f1 DNA replication: Its Signal and domains", *J Mol Biol* 172:507-521 (1984)

Dower W J, "Phage power", *Curr Biol* 2:251-253 (1992)

Ermisch, "Peptide receptors of the blood-brain barrier and substrate transport into the brain", *Progress in Brain Research*, 91:155-161 (1992)

Eshhar et al, "Chimeric T cell receptor which incorporates the anti-tumour specificity of a monoclonal antibody with the cytolytic activity of T cells: a model system for immunotherapeutical approach", *Br J Cancer Suppl*, 10:27-29 (1990)

Felici et al, "Selection of antibody ligands from a large library of oligopeptides expressed on a multivalent exposition vector", *J Mol Biol* 222:301-310 (1991)

Frenkel D., "N-terminal EFRH sequence of Alzheimer's beta-amyloid peptide represents the epitope of its anti-aggregating antibodies", *J. Neuroimmunol.*, 88:85 90 (1998)

Frenkel, D., Solomon, B. and Benhar, I. Modulation of Alzheimer's beta-amyloid neurotoxicity by site-directed single-chain antibody. *J Neuroimmunol*, 106:23-31 (2000a).

Frenkel, D., Katz, O. and Solomon, B. Immunization against Alzheimer's β-amyloid plaques via EFRH phage administration. *PNAS* 97, 21, 11455-11459 (2000b).

Frenkel, D., Kariv, N. and Solomon, B. Generation of autoantibodies towards Alzheimer's disease vaccination. *Vaccine* 19, 2615-2619 (2001).

Goldsmith et al, "Adsorption protein of bacteriophage fd: Isolation, molecular properties, and location in virus", *Biochemistry* 16:2686-2694 (1977)

Gray et al "Adsorption complex of filamentous fd virus", *J Mol Biol* 146:621-627 (1981)

Greenwood et al, "Multiple display of foreign peptides on a filamentous bacteriophage", *J Mol Biol* 220:821-827 (1991)

Gross et al, "Expression of immunoglobulin-T-cell receptor chimeric molecules as functional receptors with antibody-type specificity", *Proc Natl Acad Sci USA*, 86:10024-10028 (1989)

Harlow et al, *Antibodies: A Laboratory Manual*, Cold Spring Harbor Laboratory, Cold Spring Harbor, N.Y. (1988)

Hoess et al, "Identification of a peptide which binds to the carbohydrate-specific monoclonal antibody B3", *Gene* 128:43-49 (1993)

Holliger et al, "A conserved infection pathway for filamentous bacteriophages is suggested by the structure of the membrane penetration domain of the minor coat protein g3p from phage fd", *Structure* 5:265-275 (1997)

Iannolo et al., "Modifying filamentous phage capsid: limits in the size of the major capsid protein", *J. Mol. Biol.*, May 12;248(4):835-44 (1995)

Johansson, "Experimental models of altering the blood-brain barrier", *Progress in Brain Research*, 91:171-175 (1992)

Kay et al, "An M13 phage library displaying 38-amino-acid peptides as a source of novel sequences with affinity to selected targets", *Gene* 128:59-65 (1993)

Kensil et al., Vaccine Design: The Subunit and Adjuvant Approach (1995)

Kim et al, "Viable deletions of the M13 complementary strand origin", *Proc Natl Acad Sci USA* 78:6784-6788 (1981)

Kohler et al, "Continuous cultures of fused cells secreting antibody of predefined specificity", *Nature* 256:495-497 (1975)

Koivunen et al, "Phage libraries displaying cyclic peptides with different ring sizes: ligand specificities of the RGD-directed integrins", *Biotechnology* 13:265-270 (1995)

Krebber et al, "Co-selection of cognate-antigen pairs by selectively-infective phages", *FEBS Lett* 377:227-231 (1995)

Lane et al, "Epitope mapping using bacteriophage peptide libraries", *Curr Opin Immunol* 5:268-271 (1993)

Langer, "New methods of drug delivery", *Science*, 249:1527 (1990)

Liu et al, "Chimeric mouse-human IgG1 antibody that can mediate lysis of cancer cells", *Proc Natl Acad Sci USA* 84(10):3439-3443 (1987)

Luzzago et al, "Mimicking of discontinuous epitopes by phage displayed peptides, _. Epitope mapping of human H ferritin using a phage library of constrained peptides", *Gene* 128:51-57 (1993)

Marvin et al, "Molecular model and structural comparisons of native and mutant class filamentous bacteriophages Ff (fd, f1, M13), f1 and Ke", *J Mol Biol* 235:260-286 (1994)

Matthews et al, "Substrate phage: selection of protease substrates by monovalent phage display", *Science*, 260:1113-1116 (1993)

McCafferty et al, "Phage enzymes: expression and affinity chromatography of functional alkaline phosphatase on the surface of bacteriophage", *Protein Eng* 4:955-961 (1992)

McCafferty et al., Phage antibodies: filamentous phage displaying antibody variable domains. *Nature*, 348(6301): 552-4 (1990)

Medynski, D. Phage display: all dressed up and ready to role. *Biol Technol* 12, 1134-1136 (1994).

Meola, A., Delmastro, P., Monaci, P. et al. Derivation of vaccines from mimotopes: Immunological properties of human B virus surface antigen mimotopes displayed on filamentous phage. *J Immuno* 154, 3162-3172 (1995).

Messing J, "New M13 vectors for cloning", *Methods Enzymol* 101:20-78 (1983)

Mitchell et al., *J. Org. Chem.* (1978)

Model et al, "Filamentous Bacteriophage", in The Bacteriophages, Calendar R (ed.), Plenum Press, New York and London, Vol. 2, p. 375 (1988)

Morrison et al, "Chimeric human antibody molecules: mouse antigen-binding domains with human constant region domains". *Proc Natl Acad Sci USA* 81:6851-6855 (1984)

Moses et al, "Restructuring the bacteriophage f1 genome: Expression of gene VIII in the intergenic space", *Virology* 104:267-278 (1980)

Murphy, C. Loss of olfactory function in dementing disease. *Physiol. Behav.* 66, 177-182 (1999).

Neuberger et al, "A hapten-specific chimaeric IgE antibody with human physiological effector function", *Nature* 314: 268-270 (1985)

Ommaya, "Implantable devices for chronic access and drug delivery to the central nervous system", *Cancer Drug Delivery*, 1(2) :169-178 (1984)

Pardridge et al., "Evaluation of cationized rat albumin as a potential blood-brain barrier drug transport vector", *J. Pharmacol. Experim. Therapeutics*, 255(2):893-899 (1990)

Pardridge, "Fuel Homeostasis and the Nervous System", Edited by Vranic et al., *Plenum Press, New York*, 43-53 (1991)

Parmley et al, "Antibody-selectable filamentous fd phage vectors: affinity purification of target genes", *Gene* 73:305-318 (1988)

Rasqualini et al, "Organ targeting in vivo using phage display peptide libraries", *Nature* 380:364-366 (1996)

Sahagan et al, "A genetically engineered murine/human chimeric antibody retains specificity for human tumor-associated antigen" *J Immunol* 137:1066-1074 (1986)

Schlosshauer, "The blood-brain barrier: morphology molecules, and neurothelin", *BioEssays*, 15(5):341-346 (1993)

Schmitz et al, "Catalytic specificity of phosphotyrosine kinases Blk, Lyn, c-Src and Syk as assessed by phage display", *J Mol Biol* 260:664-677 (1996)

Scott et al, "Searching for peptide ligands with an epitope library", *Science* 249:386-390 (1990)

Smith G P "Surface display and peptide libraries", *Gene* 128:1-2 (1993)

Solomon, B. and Frenkel, D. Vaccination for the prevention and treatment of Alzheimer's disease. *Drugs of Today*, 36(9), 655-663 (2000).

Sparks et al, "Identification and characterization of Src SH3 ligands from phage-displayed random peptide libraries", *J Biol Chem* 269:23853-23856 (1994)

Sugimoto et al, "Studies on bacteriophage fd DNA. IV. The sequence of messenger RNA for the major coat protein gene", *J Mol Biol* 111:487-507 (1977)

Sun et al, "Chimeric antibody with human constant regions and mouse variable regions directed against carcinoma-associated antigen 17-1A", *Proc Natl Acad Sci USA* 84:214-218 (1987)

Tam et a., *J. Am. Chem. Soc.*, 102:6117 (1980)

Van Wezenbeek et al, "Nucleotide sequence of the filamentous bacteriophage M13 DNA genome: comparison with phage fd", *Gene* 11:129-148 (1980)

Willis et al., "Immunological properties of foreign peptides in multiple display on a filamentous bacteriophage", *Gene* 128:79-83 (1993)

Wrighton et al, "Small peptides as potent mimetics of the protein hormone erythropoietin", *Science* 273:458-463 (1996)

Zacher et al, "A new filamentous phage cloning vector: fd-tet", *Gene* 9:127-140 (1980)

Zuercher, A. W., Miescher, S. M., Voge, M., Rudolf, M. P., Stadler, M. B. and Stadler, B. M. Oral anti-IgE immunization with epitope-displaying phage. *Eur. J. Immunol.* 30, 128-135 (2000).

What is claimed is:

1. An isolated molecule comprising the antigen binding portion of an antibody directed against an epitope spanning the β-secretase cleavage site of amyloid precursor protein (AβPP) and that blocks β-secretase cleavage of AβPP.

2. The molecule of claim 1, which is a monoclonal antibody.

3. The molecule of claim 1, which is a single chain antibody.

4. The molecule of claim 1, which is a humanized antibody.

5. The molecule of claim 1, wherein said AβPP is the AβPP found in the Swedish mutation of Alzheimer's disease.

6. The molecule of claim 1, wherein said epitope is present in the amino acid sequence of SEQ ID NO:5.

7. The molecule of claim 1, wherein said epitope is present in residues 1 to 8 of SEQ ID NO:1.

8. The molecule of claim 7, wherein the residue at position 6 of SEQ ID NO:1 is Met.

9. The molecule of claim 7, wherein the residue at position 6 of SEQ ID NO:1 is Leu.

10. A method for inhibiting β-secretase cleavage of AβPP, comprising contacting AβPP with the molecule of claim 1, in the presence of β-secretase to inhibit β-secretase cleavage of AβPP.

11. A method of inhibiting formation of Aβpeptide in a subject, comprising administering to the subject an effective amount of a molecule in accordance with claim 1.

12. The molecule of claim 1, wherein said molecule comprises a display vehicle and said antigen binding portion of an antibody displayed on said display vehicle.

13. The molecule of claim 12, wherein said display vehicle comprises a viral display vehicle displaying on its surface said antigen binding portion of an antibody.

14. The molecule of claim 13, wherein said viral display vehicle is a filamentous bacteriophage.

15. A method of inhibiting formation of Aβpeptide in a subject, comprising administering to the subject an effective amount of a molecule in accordance with claim 14.

* * * * *

SEQUENCE LISTING

```
<160> NUMBER OF SEQ ID NOS: 5

<210> SEQ ID NO 1
<211> LENGTH: 26
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa is Met or Leu.

<400> SEQUENCE: 1

Ile Ser Glu Val Lys Xaa Asp Ala Glu Phe Arg His Asp Ser Gly Tyr
1               5                   10                  15

Glu Val His His Gln Lys Leu Val Phe Phe
            20                  25

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Glu Phe Arg His
1

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Asp Ala Glu Phe Arg His Asp Ser Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Trp Val Leu Asp
1

<210> SEQ ID NO 5
<211> LENGTH: 9
<212> TYPE: PRT
<213> ORGANISM: Homo sapiens

<400> SEQUENCE: 5

Val Lys Met Asp Ala Glu Phe Arg His
1               5
```